(12) United States Patent
Huiku

(10) Patent No.: US 8,515,514 B2
(45) Date of Patent: Aug. 20, 2013

(54) COMPENSATION OF HUMAN VARIABILITY IN PULSE OXIMETRY

(75) Inventor: Matti Huiku, Espoo (FI)

(73) Assignee: Datex-Ohmeda, Inc., Madison, WI (US)

( * ) Notice: Subject to any disclaimer, the term of this patent is extended or adjusted under 35 U.S.C. 154(b) by 1339 days.

(21) Appl. No.: 12/233,251

(22) Filed: Sep. 18, 2008

(65) Prior Publication Data

US 2009/0076354 A1   Mar. 19, 2009

Related U.S. Application Data

(63) Continuation of application No. 11/068,535, filed on Feb. 28, 2005, now abandoned, and a continuation-in-part of application No. 10/077,196, filed on Feb. 15, 2002, now Pat. No. 6,882,874.

(51) Int. Cl.
*A61B 5/00* (2006.01)

(52) U.S. Cl.
USPC ........... 600/331; 600/321; 600/322; 600/323; 600/326; 600/328

(58) Field of Classification Search
USPC .................. 600/310, 321–323, 326, 328, 331
See application file for complete search history.

(56) References Cited

U.S. PATENT DOCUMENTS

| | | | |
|---|---|---|---|
| 4,086,915 A | 5/1978 | Kofsky et al. | |
| 4,933,614 A | 6/1990 | Kawata | |
| 4,968,137 A | 11/1990 | Yount | |
| 5,259,381 A * | 11/1993 | Cheung et al. | 600/323 |
| 5,278,627 A | 1/1994 | Aoyagi et al. | |
| 5,348,003 A | 9/1994 | Caro | |
| 5,355,880 A | 10/1994 | Thomas et al. | |
| 5,357,953 A | 10/1994 | Merrick et al. | |
| 5,499,627 A | 3/1996 | Steuer et al. | |
| 5,630,413 A | 5/1997 | Thomas et al. | |
| 5,692,503 A | 12/1997 | Kuenstner | |
| 5,725,480 A | 3/1998 | Oosta et al. | |
| 5,792,050 A | 8/1998 | Alam et al. | |
| 5,842,979 A | 12/1998 | Jarman | |
| 5,891,024 A | 4/1999 | Jarman et al. | |
| 5,931,779 A | 8/1999 | Arakaki et al. | |
| 6,061,581 A | 5/2000 | Alam et al. | |
| 6,073,037 A | 6/2000 | Alam et al. | |
| 6,104,938 A | 8/2000 | Huiku et al. | |
| 6,163,715 A | 12/2000 | Larsen et al. | |
| 6,421,549 B1 | 7/2002 | Jacques | |
| 7,142,901 B2 * | 11/2006 | Kiani et al. | 600/331 |
| 2002/0133068 A1 | 9/2002 | Huiku | |

FOREIGN PATENT DOCUMENTS

WO    WO 01/03577 A1    1/2001

* cited by examiner

*Primary Examiner* — Sean Dougherty
*Assistant Examiner* — Devin Henson
(74) *Attorney, Agent, or Firm* — Marsh Fischmann & Breyfogle LLP; Russell T. Manning

(57) ABSTRACT

Provided is a method of calibrating a pulse oximeter, in which the effects caused by tissue of a subject can be taken into account. A detector output signal is measured when living tissue of the subject is present between emitters and the detector in a sensor. Nominal calibration and nominal calibration characteristics are read from a memory, whereupon values for the same nominal characteristics for the sensor on living tissue of the subject are established using the detector output signal. Then, changes in the nominal calibration characteristics induced by the living tissue are calculated and a subject-specific calibration is formed by correcting the nominal calibration with the changes. Finally, the hemoglobin fractions are solved using the corrected nominal calibration.

6 Claims, 12 Drawing Sheets

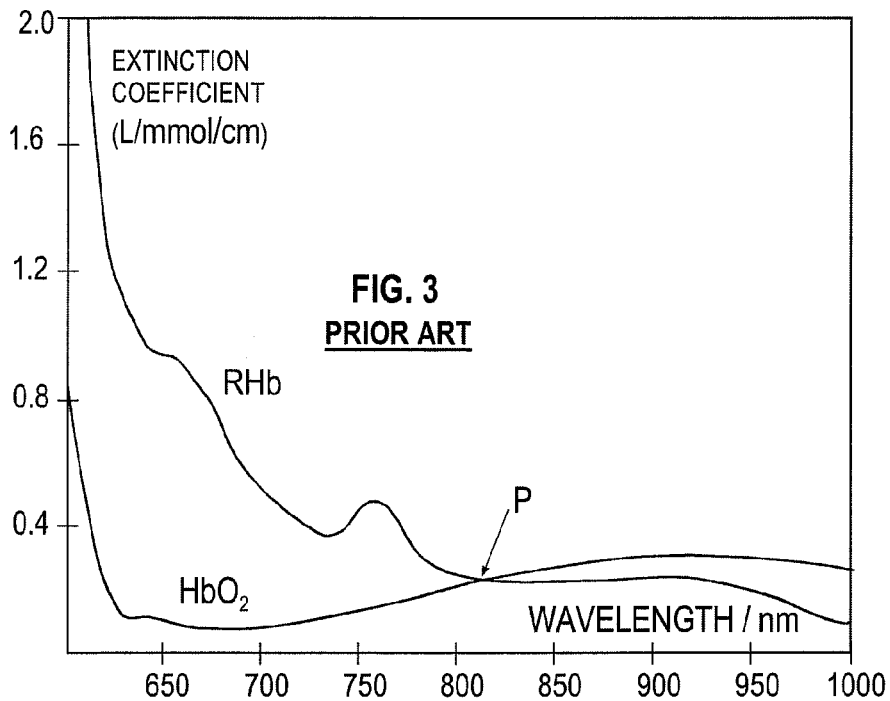
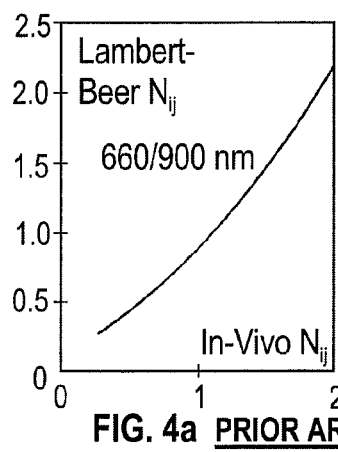 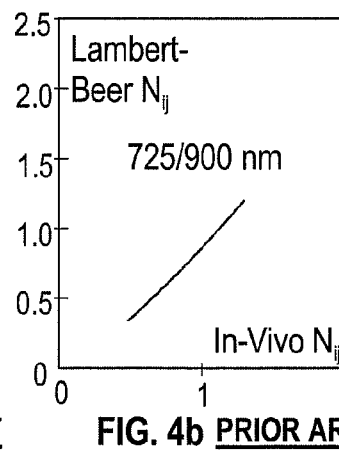 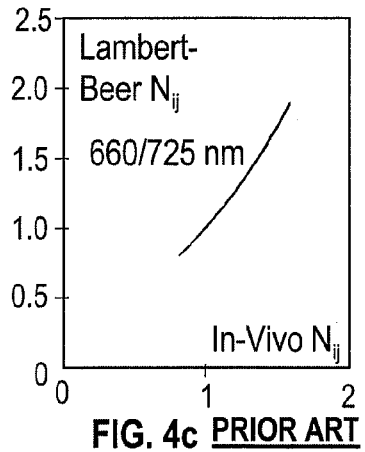
FIG. 4a PRIOR ART    FIG. 4b PRIOR ART    FIG. 4c PRIOR ART
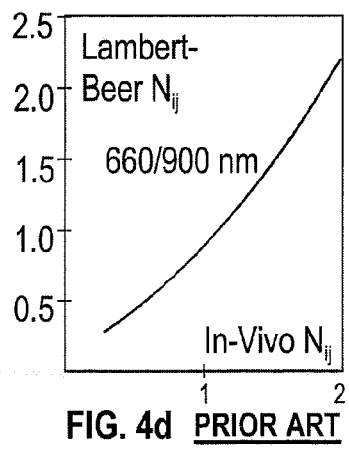 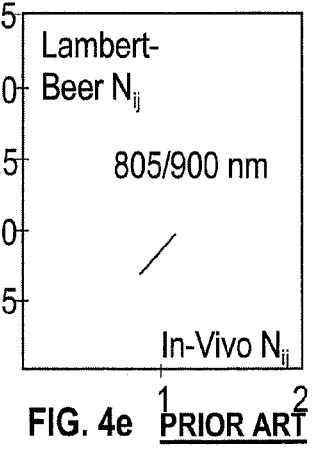 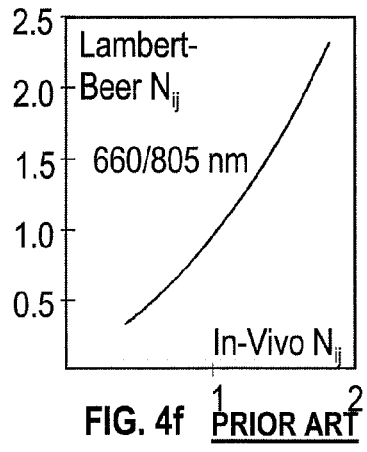
FIG. 4d PRIOR ART    FIG. 4e PRIOR ART    FIG. 4f PRIOR ART

SETTING UP

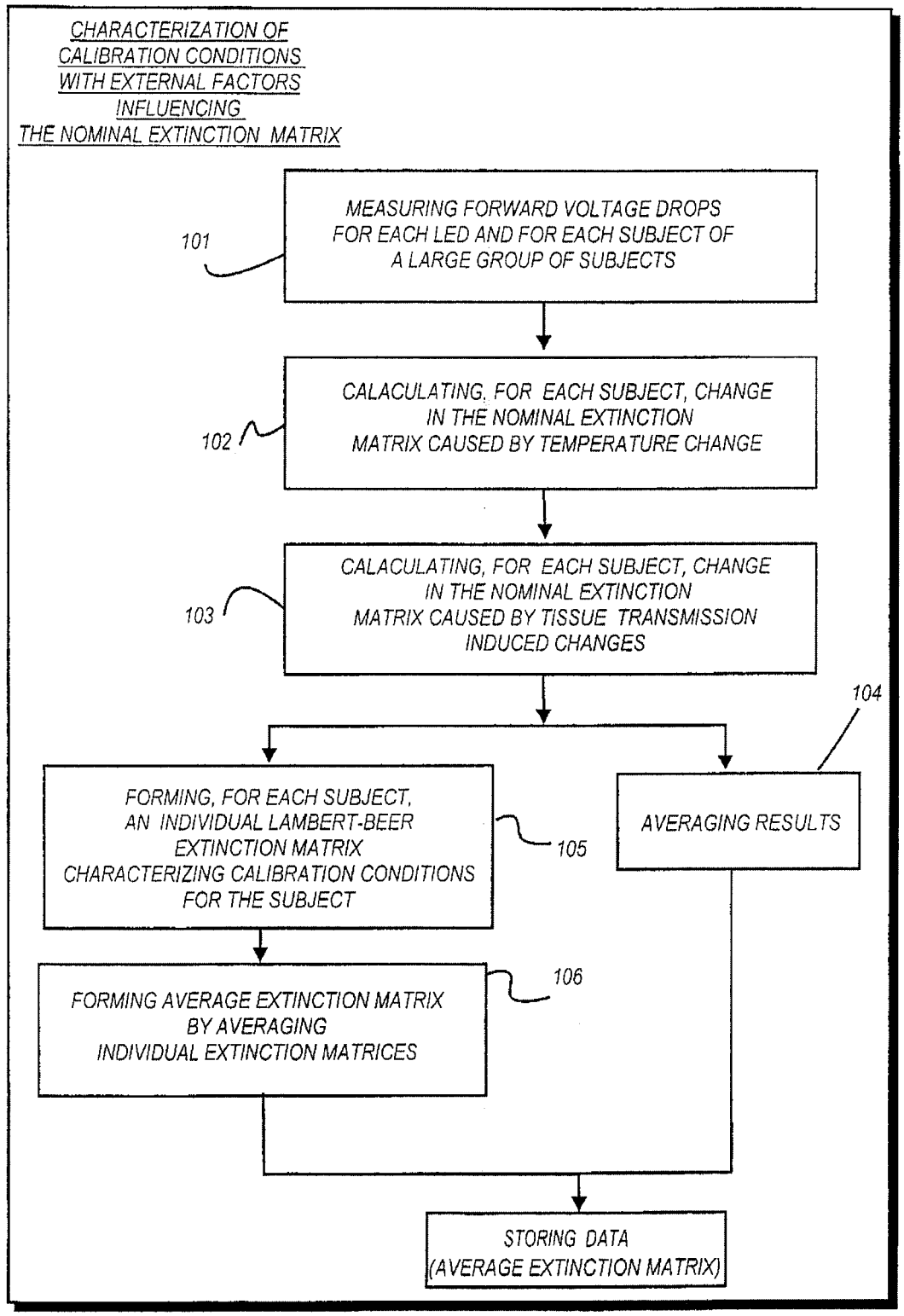
FIG. 10     SETTING UP

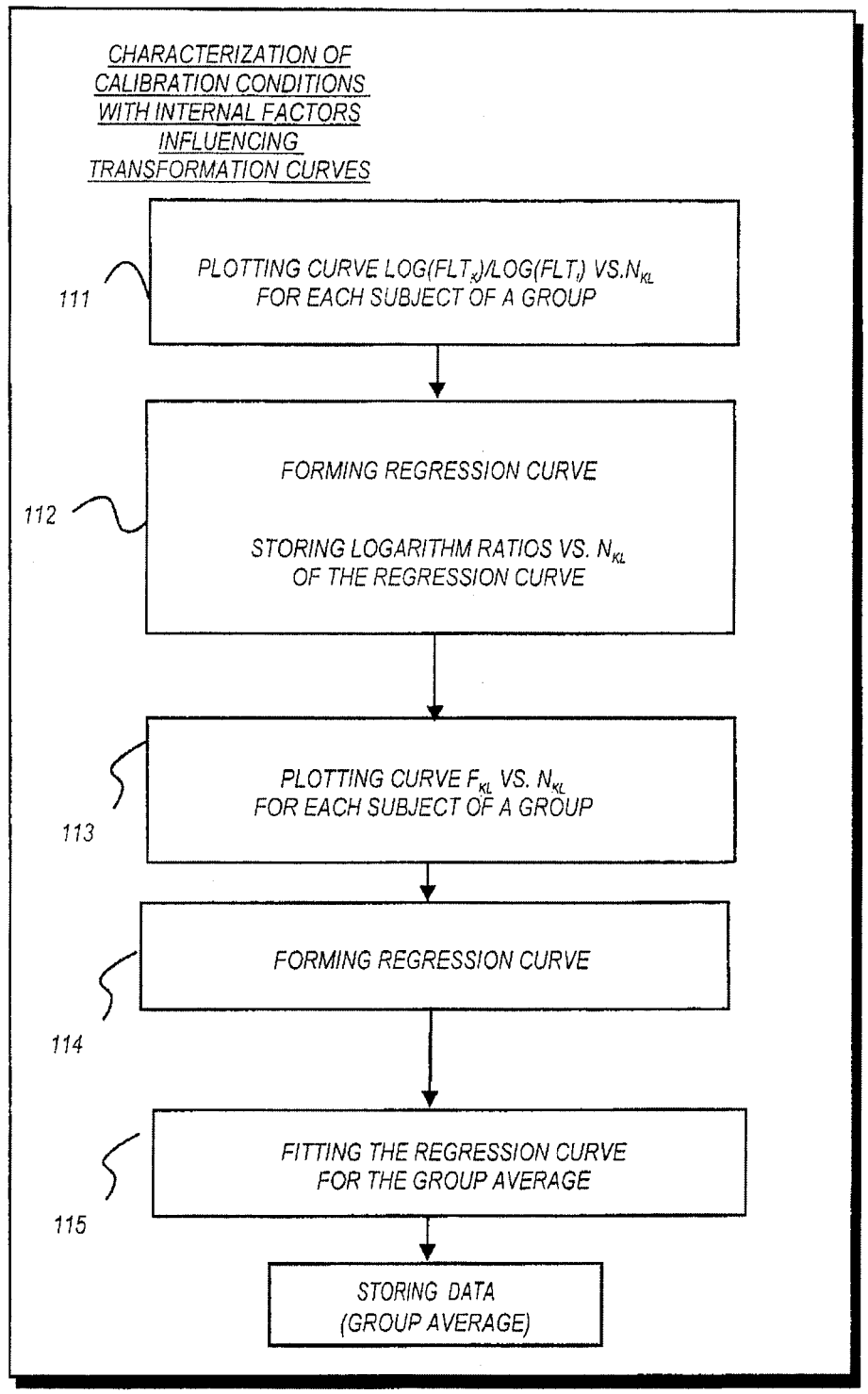
FIG. 11  SETTING UP

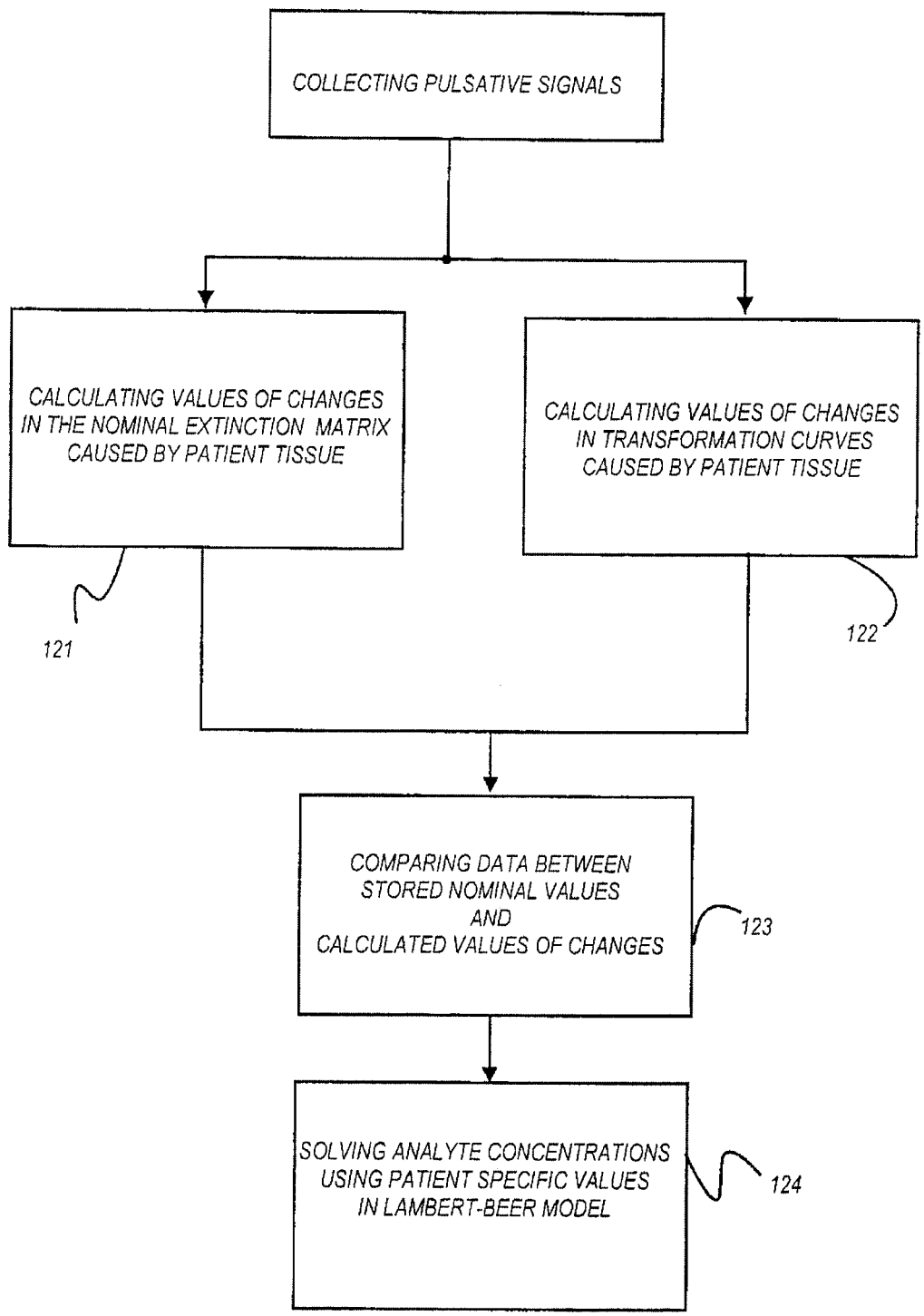
FIG. 12   IN-VIVO MEASUREMENT

COMPENSATION OF HUMAN VARIABILITY IN PULSE OXIMETRY

RELATED APPLICATIONS

This application is a continuation of U.S. patent application Ser. No. 11/068,535 filed on Feb. 28, 2005, titled "COMPENSATION OF HUMAN VARIABILITY IN PULSE OXIMETRY, which is a continuation-in-part of U.S. patent application Ser. No. 10/077,196, now U.S. Pat. No. 6,882,874 issued on Apr. 19, 2005, titled "COMPENSATION OF HUMAN VARIABILITY IN PULSE OXIMETRY", the entirety of both of which are hereby incorporated by reference.

FIELD OF THE INVENTION

The invention relates generally to pulse oximeters used to detect blood oxygenation. More specifically, the invention relates to a method for taking into account human variability in pulse oximeters. The invention further relates to a sensor allowing compensation for the inaccuracies caused by human variability, the sensor being an integral part of the pulse oximeter.

BACKGROUND OF THE INVENTION

Pulse oximetry is at present the standard of care for continuous monitoring of arterial oxygen saturation ($SpO_2$). Pulse oximeters provide instantaneous in-vivo measurements of arterial oxygenation, and thereby an early warning of arterial hypoxemia, for example.

A pulse oximeter comprises a computerized measuring unit and a probe attached to the patient, typically to a finger or ear lobe. The probe includes a light source for sending an optical signal through the tissue and a photo detector for receiving the signal after transmission through the tissue. On the basis of the transmitted and received signals, light absorption by the tissue can be determined. During each cardiac cycle, light absorption by the tissue varies cyclically. During the diastolic phase, absorption is caused by venous blood, tissue, bone, and pigments, whereas during the systolic phase there is an increase in absorption, which is caused by the influx of arterial blood into the tissue. Pulse oximeters focus the measurement on this arterial blood portion by determining the difference between the peak absorption during the systolic phase and the constant absorption during the diastolic phase. Pulse oximetry is thus based on the assumption that the pulsatile component of the absorption is due to arterial blood only.

Light transmission through an ideal absorbing sample is determined by the known Lambert-Beer equation as follows:

$$I_{out}=I_{in}e^{-\epsilon DC}, \quad (1)$$

where $I_{in}$ is the light intensity entering the sample, $I_{out}$ is the light intensity received from the sample, D is the path length through the sample, $\epsilon$ is the extinction coefficient of the analyte in the sample at a specific wavelength, and C is the concentration of the analyte. When $I_{in}$, D, and $\epsilon$ are known, and $I_{out}$ is measured, the concentration C can be calculated.

In pulse oximetry, in order to distinguish between two species of hemoglobin, oxyhemoglobin ($HbO_2$), and deoxyhemoglobin (RHb), absorption must be measured at two different wavelengths, i.e. the probe includes two different light emitting diodes (LEDs). The wavelength values widely used are 660 nm (red) and 940 nm (infrared), since the said two species of hemoglobin have substantially different absorption values at these wavelengths. Each LED is illuminated in turn at a frequency which is typically several hundred Hz.

The accuracy of a pulse oximeter is affected by several factors. This is discussed briefly in the following.

Firstly, the dyshemoglobins which do not participate in oxygen transport, i.e. methemoglobin (MetHb) and carboxyhemoglobin (COHb), absorb light at the wavelengths used in the measurement. Pulse oximeters are set up to measure oxygen saturation on the assumption that the patient's blood composition is the same as that of a healthy, non-smoking individual. Therefore, if these species of hemoglobin are present in higher concentrations than normal, a pulse oximeter may display erroneous data.

Secondly, intravenous dyes used for diagnostic purposes may cause considerable deviation in pulse oximeter readings. However, the effect of these dyes is short-lived since the liver purifies blood efficiently.

Thirdly, coatings like nail polish may in practice impair the accuracy of a pulse oximeter, even though the absorption caused by them is constant, not pulsatile, and thus in theory it should not have an effect on the accuracy.

Fourthly, the optical signal may be degraded by both noise and motion artifacts. One source of noise is the ambient light received by the photodetector. Many solutions have been devised with the aim of minimizing or eliminating the effect of the movement of the patient on the signal, and the ability of a pulse oximeter to function correctly in the presence of patient motion depends on the design of the pulse oximeter. One way of canceling out the motion artefact is to use an extra wavelength for this purpose.

A further factor affecting the accuracy of a pulse oximeter is the method used to calibrate the pulse oximeter. Usually the calibration is based on extensive empirical studies in which an average calibration curve is determined based on a high number of persons. By means of this calibration curve, which relates the oxygen saturation of blood to pulse oximeter signals, the average difference between the theory and practice (i.e. in-vivo measurements) is taken into account. The calibration curve typically maps the measured in-vivo signal to a corresponding $SpO_2$ value.

Pulse oximeters, however, can also utilize the Lambert-Beer model for calculating the concentrations of the different Hb species. In this method of calibration, the measurement signals must first be transformed into signals applicable to the Lambert-Beer model for calculation. This transformation constitutes the calibration of the pulse oximeter, since it is the step which adapts the in-vivo signals to the Lambert-Beer theory, according to which the pulse oximeter is designed to operate. Thus, the calibration curves can also be in the form of transformations used to adapt the actual in-vivo measurements to the Lambert-Beer model.

Transformations are discussed for example in U.S. Pat. No. 6,104,938, which discloses a calibration method based on the absorption properties of each hemoglobin component, i.e. on the extinction coefficients of blood. In this method, the effective extinction coefficients are determined for each light signal via a mathematical transformation from the extinction coefficients according to the Lambert-Beer theory.

Below, the solution according to the invention is discussed with reference to a pulse oximeter utilizing the above-mentioned transformations and four different wavelengths. As mentioned above, U.S. Pat. No. 6,104,938 discloses a pulse oximeter utilizing the transformations.

FIG. 1 is a block diagram of a pulse oximeter utilizing four different wavelengths. Light from four different LEDs 10a, 10b, 10c, and 10d, each operating at a respective wavelength, passes into patient tissue, such as a finger 11. The light propagated through or reflected from the tissue is received by a photodetector 12, which converts the optical signal received into an electrical signal and feeds it to an input amplifier 13. The amplified signal is then supplied to a control unit 14, which carries out calculation of the amount of the Hb-derivatives in the blood. The control unit further controls the LED drive 15 to alternately activate the LEDs. As mentioned above, each LED is typically illuminated several hundred times per second.

When each LED is illuminated at such a high rate as compared to the pulse rate of the patient, the control unit obtains a high number of samples at each wavelength for each cardiac cycle of the patient. The value of these samples (i.e. the amplitude of the received signal) varies according to the cardiac cycle of the patient, the variation being caused by the arterial blood, as mentioned above. The control unit 14 therefore utilizes four measurement signals, as shown in FIG. 2, each being received at one of the wavelengths.

In order for variations in extrinsic factors, such as the brightness of the LEDs, sensitivity of the detector, or thickness of the finger, to have no effect on the measurement, each signal received is normalized by extracting the AC component oscillating at the cardiac rhythm of the patient, and then dividing the AC component by the DC component of the light transmission or reflection. The signal thus obtained is independent of the above-mentioned extrinsic factors. Thus in this case the control unit utilizes four normalized signals, which are in the following denoted with $$dA_i = \frac{AC_i}{DC_i},$$

where i is the wavelength in question (in this basic embodiment of the multi-wavelength pulse oximeter i=1, 2, 3, 4), $AC_i$ is the AC component at wavelength i, and $DC_i$ is the DC component at wavelength i. The signals $dA_i$ are also referred to below as modulation signals. The modulation signals thus indicate how absorption is affected by the arterial blood of the patient.

The above-described measurement arrangement corresponds to a conventional four-wavelength pulse oximeter. The operation of the pulse oximeter is discussed in more detail below.

The theory of pulse oximetry is generally presented as being based on the Lambert-Beer Law. According to this theory, light transmission through the tissue at each wavelength is exponentially dependent on the absorbance of the tissue (Eq. 1). This theory is generally accepted and established as a good model for pulse oximetry.

Next to be discussed is the theory and formalism on which the method of the invention is based.

According to the Lambert-Beer theory and for a system of two analytes, the signals described above can be presented as follows:

$$dA_1 = dA \times (\epsilon_1^{HbO_2} \times HbO_2 + \epsilon_1^{RHb} \times RHb)$$

$$dA_2 = dA \times (\epsilon_2^{HbO_2} \times HbO_2 + \epsilon_2^{RHb} \times RHb)$$

$$dA_3 = dA \times (\epsilon_3^{HbO_2} \times HbO_2 + \epsilon_3^{RHb} \times RHb)$$

$$dA_4 = dA \times (\epsilon_4^{HbO_2} \times HbO_2 + \epsilon_4^{RHb} \times RHb)$$

$$RHb = 1 - HbO_2$$

where dA is a common factor which depends on the absolute values, i.e. inter alia on the total amount of hemoglobin, $\epsilon_i^{HbO_2}$ is the extinction coefficient of oxyhemoglobin at wavelength i (i=1–4), $\epsilon_i^{RHb}$ is the extinction coefficient of deoxyhemoglobin at wavelength i, $HbO_2$ is the concentration fraction of oxyhemoglobin, and RHb is the concentration fraction of deoxyhemoglobin.

Using a matrix notation, the above dependencies can be expressed for a system of n wavelengths and n analytes as follows:

$$\begin{pmatrix} dA_1 \\ dA_2 \\ \ldots \\ dA_n \end{pmatrix} = C * \begin{pmatrix} \varepsilon_{11} \ldots \varepsilon_{1n} \\ \varepsilon_{21} \ldots \varepsilon_{2n} \\ \ldots \\ \varepsilon_{n1} \ldots \varepsilon_{nn} \end{pmatrix} \cdot \begin{pmatrix} HbX_1 \\ HbX_2 \\ \ldots \\ HbX_n \end{pmatrix}, \quad (2)$$

where $dA_i$ is the differential change in absorption (i.e. the modulation signal) at wavelength $\lambda_i$, $\epsilon_{ij}$ is the extinction coefficient of the hemoglobin derivative $HbX_j$ at wavelength $\lambda_i$, and the constant C accounts for the change of units to fractional percentages of the concentrations of the analytes $HbX_j$.

FIG. 3 shows the extinction coefficients ($\epsilon^{HbO_2}$ and $\epsilon^{RHb}$) of oxyhemoglobin ($HbO_2$) and deoxyhemoglobin (RHb) as a function of the wavelength. Point P shown in the figure is the isobestic point of oxyhemoglobin ($HbO_2$) and deoxyhemoglobin (RHb). The point has the special property that the modulation signal at the wavelength in question does not depend on the respective proportions (relative concentrations) of the hemoglobin species. Thus at the wavelength of point P the effect of the relative concentrations of oxyhemoglobin and deoxyhemoglobin on the result of the measurement is nil. It should be noted, however, that the modulation signal is independent of the relative concentrations only, not of the absolute concentrations. Thus, the absolute amount of the hemoglobin species has an effect on the result of the measurement.

As is known, there is a difference between the Lambert-Beer theory and the practical measurements. The difference is due to the fact that the Lambert-Beer theory does not take into account the scattering and non-homogeneity of the tissue, whereas the actual extinction coefficients are also dependent on the scattering of light caused by the tissue and blood, and on the combined effect of absorption and scattering. The larger the proportion of the attenuation caused by absorption and scattering, the larger is the correction needed between the actual and the theoretical (non-scatter) domains. This correction between these two domains can be represented by the transformation curves discussed above, by means of which the actual in-vivo measurements are mapped to the Lambert-Beer model.

The transformation can be expressed, for example, as follows:

$$N_{kl}^{L-B} = g_{kl}^{-1}(N_{kl}^{in-vivo}) \text{ where } N_{kl} = \frac{dA_k}{dA_l}, \quad (3)$$

is the modulation ratio (the superscript indicating the domain) and the subscripts k and l indicating the wavelengths in question), and g is the transformation, for instance in the form of a polynomial function, transforming the L-B N-values to the corresponding N-values in the in-vivo domain. The $g^{-1}$ in Eq. 3 is the inverse transformation, i.e. the inverse function, for transforming the measured in-vivo values to the ideal, non-scatter, values in the L-B domain FIGS. 4a to 4f illustrate the average transformation curves measured for a pulse oximeter, where the two wavelengths for measuring the two species of hemoglobin are 660 nm and 900 nm and the third wavelength is either 725 nm or 805 nm. FIGS. 4a to 4c illustrate the transformation curves for a pulse oximeter with the third wavelength being 725 nm, and FIGS. 4d to 4f illustrate the transformation curves for a pulse oximeter with the third wavelength being 805 nm. Each curve shows the Lambert-Beer $N_{k,l}$ as a function of the in-vivo $N_{kl}$ at wavelengths k and l.

FIG. 5 is a flow diagram describing the general measurement principle described in U.S. Pat. No. 6,104,938. In this method, the above-mentioned $N_{kl}^{in\text{-}vivo}$ values are first determined from the $dA_i$ values measured (step 51). The average transformations $g_{kl}$ are then used to convert the measured in-vivo values to values $N_{kl}^{L\text{-}B}$, which can be used in the ideal Lambert-Beer model (step 52). Other input values needed for the Lambert-Beer model are also determined (step 53). In practice these input values are the ideal (nominal) extinction coefficients of the analytes to be measured, the extinction coefficients being given for the center wavelengths used in the measurement. The converted transformation values and the nominal input values (i.e. nominal extinction coefficients) are then used according to the Lambert-Beer model to calculate the concentrations of the desired analytes (step 54). Thus in this approach the in-vivo values $N_{kl}^{in\text{-}vivo}$ measured from the tissue are converted to the ideal in-vitro (cuvette) environment, where the ideal oximetry model (i.e. the Lambert-Beer model) is applied to yield the desired concentrations.

In the standard two wavelength pulse oximetry the prior art technique is to map the modulation ratio $N_{kl}^{in\text{-}vivo}$ directly to the SpO2 percentage measured. In this simple case the transformation is not necessary, though the transformation technique together with the solution in the Lambert-Beer domain can be utilized as well.

There are two basic ways to determine the average transformation, a theoretical approach and an empirical approach. In the empirical approach the measurements are made in the tissue by taking blood samples and measuring the actual proportions of the hemoglobin species and then determining the value of $N_{kl}^{L\text{-}B}$ on the basis of the measured proportions. The transformation is then obtained as the relationship between the values based on the blood samples and the values given by empirical measurements as measured by the pulse oximeter. The theoretical approach, in turn, is based on a known tissue model, which takes into account the characteristics of the tissue as referred to above, which are ignored in the Lambert-Beer model. A first value is determined for in-vivo $N_{kl}$ by means of the tissue model and a second value on the basis of the Lambert-Beer model. The tissue parameters of the model are determined so that the known 2-wavelength calibration (so-called R-curve) is reproduced. Then using these tissue parameters and the wavelength dependence of the tissue model, the relation of the in-vivo $N_{kl}$ and the Lambert-Beer $N_{kl}$ is extrapolated to other wavelengths in order to obtain the transformations at these new wavelengths. Thus in the theoretical approach no new empirical measurements are made.

In practice the transformation can be a quadratic equation yielding a correction of the order of 20 percent to the measured $N_{kl}^{in\text{-}vivo}$ value, for example. As discussed below, the transformation data (i.e. the transformation curves) are preferably stored in numeric form in the pulse oximeter or the sensor. The number of transformation curves stored in the pulse oximeter can vary, depending on the number of wavelengths used, for example. Typically there is a transformation curve for each wavelength pair.

As mentioned above, the accuracy of a pulse oximeter utilizing an average transformation is not necessarily sufficient, especially if analytes which are weak absorbers are to be measured or if two analytes absorb similarly, whereby it is difficult to distinguish the said analytes from each other.

Further, each patient (i.e. subject of the measurement) has a calibration curve of his or her own, which deviates from the average calibration curve calculated on the basis of a high number of patients. This is due to the fact that for each patient the characteristics of the tissue through which light is transmitted deviate from those of an average patient.

This causes one drawback of the current pulse oximeters; they are incapable of taking this human variability into account. Human variability here refers to any and all factors causing patient-specific variation in the calibration curve, including time-dependent changes in the calibration curve of a single patient. As discussed in the above-mentioned U.S. Patent, subject-dependent variation can also be seen as an effect of a third substance, such as a third hemoglobin species in the blood. However, the variation can also be interpreted as a subject-dependent change in the calibration curve of the pulse oximeter.

Without compensation for human variability, the accuracy of current pulse oximeters is about ±2% SpO2. However, in multi-wavelength applications in general, and especially if weak absorbers, such as COHb, are to be measured, the human variability represents a much more serious problem. Therefore, techniques of compensation for these inaccuracies are called for.

It is an objective of the invention to bring about a solution by means of which the effects caused by the tissue of the subject can be taken into account when a pulse oximeter is calibrated. In other words, it is an objective of the present invention to create a pulse oximeter which can take into account the differences caused by an individual subject as compared to the average calibration or transformation curve which the current pulse oximeter relies on.

A further objective of the invention is to bring about a general-purpose solution for the compensation of inaccuracies caused by human variability in pulse oximetry, a solution which is not limited to the particular general calibration method employed in the pulse oximeter, but which can be applied to any pulse oximeter regardless of its current built-in calibration method.

SUMMARY OF THE INVENTION

These and other objectives of the invention are accomplished in accordance with the principles of the present invention by providing a mechanism by means of which the subject-specific deviation in the tissue-induced effects on the accuracy of the pulse oximeter can be taken into account. Thus, the accuracy of the pulse oximeter is improved by taking into account the subject-specific light transmission through the tissue, and changing the values input to the ideal model, i.e. the nominal transformation and the nominal extinction coefficients, on the basis of the measurement to compensate for the subject-specific changes.

In the method of the invention, the effect of tissue is taken into account and the inaccuracies caused by subject-specific variation in that effect are compensated for. This is implemented by defining a nominal calibration for the apparatus and making initial characterization measurements in order to define the characteristics which describe the conditions under which the nominal calibration has been defined. Reference data indicating the characteristics are stored for subsequent in-vivo measurements in which light transmission through the actual tissue of the patients is measured. (Initial characterization measurements here refer to the measurements performed before the apparatus is taken into use. The term is used to refer to A. the characterization measurements without tissue, i.e. mainly characterization of the optical components of the sensor, and B. the characterization measurements of the tissues in volunteered or hospitalized subjects for which the nominal calibration of the oximeter is established.) Individual subject-specific calibration is then defined based on the nominal calibration, and the reference data created in connection with the initial characterization measurements in the subject group in the nominal calibration, the in-vivo measurements in an individual patient and the in-vivo characterization measurements, defining the tissue characteristics of the individual patient in the in-vivo measurement. (In-vivo characterization measurements here refer to the characterizations performed when the apparatus is in actual use.) The in-vivo characterization also includes a step in which the information from the optical properties of the particular sensor, used in the in-vivo measurement of the individual patient, is read into the oximeter. Thus, the inaccuracies are eliminated by means of comparing the optical properties of the sensors and the characteristics of the tissues in the calibration measurements and the in-vivo measurements in the individual patient. Thus the initial characterization measurements are used to create the reference data so that light transmission measured subsequently through the tissue of a subject can be used to correct the nominal calibration for that particular subject.

Thus in one aspect the invention provides a method for compensating for subject-specific variability in an apparatus intended for non-invasively determining the amount of at least two light absorbing substances in the blood of a subject and being provided with emitter means for emitting radiation at a minimum of two different wavelengths and with detector means for receiving the radiation emitted, the method comprising the steps of carrying out initial characterization measurements, said measurements to include the measuring of radiation received by the detector, based on the initial characterization measurements, establishing nominal characteristics describing conditions under which the nominal calibration is established, calibrating the apparatus using a nominal calibration, storing reference data indicating the nominal characteristics and nominal calibration, performing in-vivo characterization measurements on a living tissue, said measurements to include the measuring of radiation emitted through the tissue and received by the detector means is measured, performing simultaneously with the in-vivo characterization measurement measurements, wherein the pulsative light absorption is measured, based on the in-vivo measurements, establishing characteristics describing conditions under which the in-vivo measurement is done, based on the in-vivo characteristics and the reference data stored, determining tissue-induced changes in the nominal characteristics, and compensating for subject-specific variation in the in-vivo measurements by correcting the nominal calibration on the basis of the tissue-induced changes.

In a preferred embodiment of the invention the method is divided in two steps so that the first step compensates for the inaccuracies caused by tissue-induced and sensor-induced wavelength shift and the second step compensates for the inaccuracies caused by internal effects occurring in the tissue. The first step is then used to correct the extinction coefficients of the blood analytes to be measured, and the second step is used to correct the average transformation stored in the pulse oximeter.

In a further preferred embodiment of the invention the effect of the temperature is also compensated for in connection with the first step.

The method is not limited to pulse oximeters explicitly using the transformations, but can be applied to any pulse oximeter. However, the method is preferably applied to a pulse oximeter based on a transformation, since in a preferred embodiment the method is implemented by carrying out changes separately in the transformation and in the extinction coefficients.

In another aspect, the invention provides an apparatus for non-invasively determining the amount of at least two light absorbing substances in the blood of a subject, the apparatus comprising emitter means for emitting radiation at a minimum of two different wavelengths, detector means for receiving said radiation at each of said wavelengths and producing at least two electrical output signals, first signal processing means for processing said output signals and producing a modulation signal for each wavelength, whereby each modulation signal represents the pulsating absorption caused by the arterialized blood of the subject, second signal processing means for applying a predetermined calibration on said modulation signals, whereby transformed modulation signals applicable in the Lambert-Beer model are obtained, memory means for storing and reading reference data indicating nominal characteristics under which said predetermined calibration has been applied, first compensation means, operatively connected to the memory means, for determining tissue-induced changes in the nominal characteristics, second compensation means, operatively connected to the first compensation means, for defining a subject-specific calibration by correcting the predetermined calibration on the basis of the tissue-induced changes, and calculation means, responsive to the second compensation means, for determining said amounts, and display means.

In a still further aspect, the invention provides a sensor for collecting measurement data for a pulse oximeter intended for non-invasively determining the amount of at least two light absorbing substances in the blood of a subject, the sensor comprising emitter means for emitting radiation at a minimum of two different wavelengths, detector means for receiving said radiation at each of said wavelengths and for producing at least two electrical output signals, storage means including nominal calibration and reference data indicating nominal characteristics describing calibration conditions of the pulse oximeter, said data allowing apparatus connected to the sensor to determine tissue-induced changes in the nominal characteristics when radiation is emitted through said tissue.

The invention relates to a method of calibrating a pulse oximeter, in which the effects caused by tissue of a subject can be taken into account. A detector output signal is measured when living tissue of the subject is present between emitters and the detector in a sensor. Nominal calibration and nominal calibration characteristics are read from a memory, whereupon values for the same nominal characteristics for the sensor on living tissue of the subject are established using the detector output signal. Then, changes in the nominal calibration characteristics induced by the living tissue are calculated and a subject-specific calibration is formed by correcting the nominal calibration with the changes. Finally, the hemoglobin fractions are solved using the corrected nominal calibration. The invention also relates to a pulse oximeter having pre-stored data in a memory comprising data of initial characterization measurements, data of nominal characteristics describing calibration conditions under which a predetermined calibration of the apparatus has been applied, and data of nominal calibration and nominal calibration characteristics. An extinction coefficient compensation block is operatively connected to the first signal processing means and to the memory for reading data, said block comprising first calculation means adapted to correct the nominal characteristics of the sensor on living tissue of the subject. A transformation compensation block is operatively connected to the first signal processing means for receiving the DC signals and to the memory for reading data, said block comprising second calculation means adapted to correct the transformation values based on the changes in the DC signals induced by tissue of the subject. Alternatively, said data may be stored in the sensor part of the pulse oximeter. Preferred embodiments of the invention are discussed in more detail below.

BRIEF DESCRIPTION OF THE DRAWINGS

In the following, the invention and its preferred embodiments are described more closely by referring to the appended drawings, wherein:

FIG. 3 shows the extinction coefficients of two different species of hemoglobin as a function of wavelength;

FIG. 4a to 4f illustrate the average transformation curves for two different pulse oximeters;

FIG. 10 is a block diagram depicting different steps of the first stage in FIG. 9;

FIG. 11 is a block diagram depicting different steps of the second stage in FIG. 9;

FIG. 12 shows compensation of human variability in the in-vivo measurement;

DESCRIPTION OF THE INVENTION

Guidelines for Implementing the Invention

Figure 1:
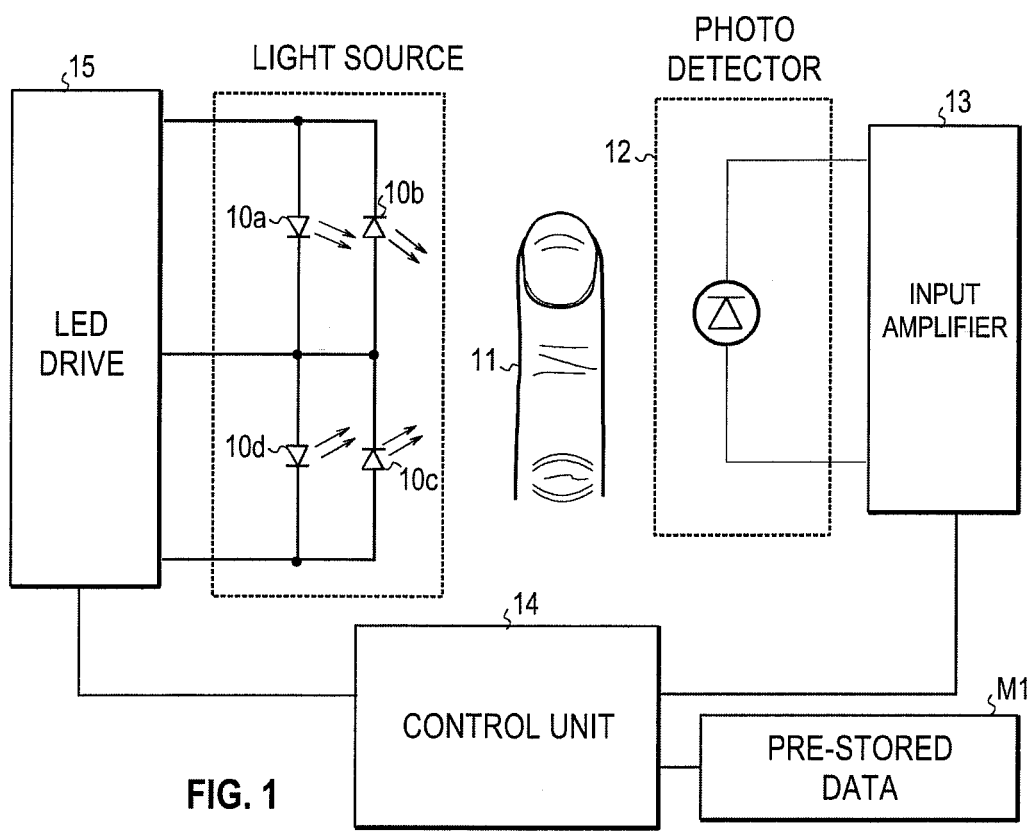
FIG. 1 illustrates the basic embodiment of a pulse oximeter according to the present invention.
Figure 2:
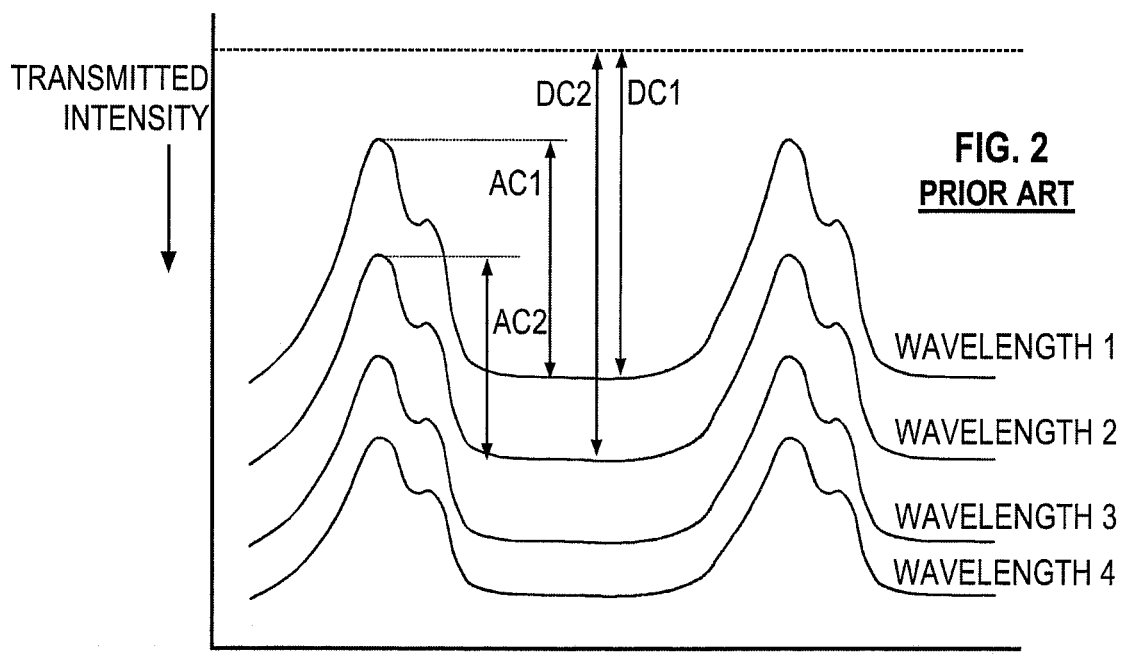
FIG. 2 illustrates the signals utilized in the pulse oximeter of FIG. 1.

The method of the present invention is implemented in the control unit of the pulse oximeter on the basis of the four modulation signals described above, i.e. the novelty of the system resides within the control unit itself. However, to be able to perform the self-calibration in conjunction with each patient, the control unit requires some pre-calculated data, which is stored in the memory of the pulse oximeter. Instead of being stored in conjunction with the control unit, this data, or at least part of it, can also be stored in the sensor part of the pulse oximeter. The sensor part, including at least the LEDs and the photo detector, is connected to the signal processing part, which includes the control unit. Consequently, depending on the overall configuration, the novelty can also reside partly in the sensor.

Human tissue can influence the accuracy of a pulse oximeter by two different mechanisms. First a direct wavelength shift is caused in the LED emission due to the filtering effect of the tissue. Namely, on one side of the LED center wavelength the absorption may be larger than on the other, whereby the center wavelength of the transmitted or reflected light is effectively shifted towards the region with smaller absorption. The second mechanism is a subtle one. It arises from the fact that the arterial blood is in interaction with the surrounding tissue, which can either increase or decrease the effective path length through the arterial blood layer. The first mechanism is in this context termed the external mechanism, since it affects factors external to the tissue (wavelength). The second mechanism is called the internal mechanism, as it is caused by internal factors in the tissue itself.

Therefore, adding two compensating processes to the prior art mechanism preferably compensates for the subject-specific variations in the influence of tissue. In other words, prior art nominal calibration is corrected with two compensating process. The first process attends to the subject-specific variation in the external mechanism, and the second process attends to the subject-specific variation in the internal mechanism. The first process preferably controls the extinction coefficients to be input to the Lambert-Beer model, while the second process preferably controls the value of the transformation used to transform the modulation ratios $N_{kl}^{in\text{-}vivo}$ to the Lambert-Beer model $N_{kl}^{L\text{-}B}$. The linear equations with the unknown analyte concentrations are then solved in the Lambert-Beer model, as in the prior art method. The degree of these compensations is determined by DC light transmission through the tissue (the measured DC signal), measured both in the initial characterization and in-vivo characterization conditions.

a) Compensating for Tissue Filter Effect to Nominal Extinction Coefficient Values Nominal extinction coefficients determined without tissue must be corrected by measuring DC light transmission through tissue and determining the optical characteristics of the particular sensor without tissue. Based on the without-tissue sensor characteristics new nominal extinction coefficients without tissue for the particular in-vivo sensor are calculated. Then in the actual in-vivo measurement, subject-specific extinction coefficients, i.e. individual extinction coefficients of a patient, are calculated for each patient and for each time moment at which a change of tissue properties in-vivo has been observed. Finally, based on the without-tissue optical properties and the in-vivo tissue properties, the final extinction coefficient values are found continuously in real-time, whereupon said values are input to the Lambert-Beer model.

We next discuss the mechanisms by which tissue changes the extinction coefficients (external mechanism) and the transformation functions (internal mechanism). We introduce a parameter called the Functional Light Transmission $(FLT)_i$ at a wavelength i, since it is used below in order to make all $DC_i$ values (measured at varying LED emission powers at the four discrete wavelengths i) comparable to each other. Using DC values comparable to each other is in practice a prerequisite for unveiling the real effect of the tissue on the measurements and the characteristics of the tissue. In order to obtain the comparable units, the DC light transmission for each LED channel (wavelength) is first measured at a certain emitter drive current, and the measured DC value is then reduced in the preamplifier to a detector current, which is normalized to an emitter current value of 1 mA. When measured without the tissue in the probe, this result is called the Current Transfer Ratio (CTR) of the probe. CTR characterizes the sensor design and the efficiency of the light transmission from the emitters to the detector. It is usually of the order of a few microAmps (of detector current) per one milliAmp (of LED current). Now the tissue (e.g. a finger) is inserted into the probe and the CTR is again measured. This result is now called the Functional Current Transfer Ratio (FCTR) because it is the CTR measured under conditions of the function of the pulse oximeter, i.e. when the tissue is in place in the probe. The $FLT_i$ is then calculated for each emitter (wavelength) as follows:

$$FLT(\text{emitter}\#k) = FCTR(1mA\text{-emitter-current})/CTR(1mA\text{-emitter-current})$$

Next the CTR and the FCTR concepts will be linked to the Lambert-Beer absorption model and to the actual measured intensities in the pulse oximeter. The CTR obviously describes how the external probe design factors, such as the color and geometry of the probe, affect the light transmission to the detector. On the other hand, the FLT can be associated with the true transmission through the tissue in units which are normalized to the emitter efficiency. Therefore, Eq. 1 can be written in a slightly different form, as it is often written in transport theory:

$$I = I_0 \exp(-\alpha^* d) = I_0 \exp(-\alpha_{int}^* d) \exp(-\alpha_{ext}^* d') \quad (4),$$

where d is the tissue thickness and $\alpha$ is an effective absorption coefficient. The above equation has been divided into two components. The attenuation factor with $\alpha_{int}$ accounts for all internal absorption effects, such as blood and can be associated to the FLT-value as the FLT equals one when no tissue (no internal attenuation) is in the probe, and the factor with $\alpha_{ext}$ accounts for all external attenuations, such as geometrical factors and multiple surface reflections without light penetration into the tissue, and can be associated with the CTR of the probe. (The term d' denotes the 'phantom' absorption thickness parameter for the external effects.) The term $\alpha_{ext}$ is mainly a SpO2 probe design issue which does not influence the measurement accuracy as such, and thus it need not to be compensated for by any means. The FLT at wavelength k can now be defined as:

$$FLT_k = \frac{I}{I_0 \exp(-\alpha_{ext} * d')} = \exp(-\alpha_{int} * d) = FCTR_k / CTR_k. \quad (5)$$

The FLT thus describes light attenuation caused by the tissue, and it can be related to the DC light transmission in the pulse oximeter.

In the following the compensations are discussed in more detail. The compensation of subject-variability causing wavelength shift type interference (i.e. external mechanism) is discussed first.

In the Lambert-Beer model (see Eq. 2) the effective extinctions $\epsilon_{ij}^{\textit{effective}}$ for broadband emitters, such as LEDs, can be calculated as follows:

$$\varepsilon_{ij}^{\textit{effective}} = \frac{1}{W} \int_{\Delta\lambda} \varepsilon_j(\lambda) * LED_i(\lambda(T)) * DET(\lambda) * \text{tissue}(\lambda) \partial\lambda, \quad (6)$$

where the integration is over the LED emission spectrum $LED_i(\lambda(T))$, $DET(\lambda)$ represents the spectral sensitivity of the detector, tissue($\lambda$) is the spectral transmission of light through the tissue, $\epsilon_j(\lambda)$ is the spectral extinction of the analyte in question, T is the temperature, and W=∫LED*DET*tissue*∂$\lambda$ represents a normalization factor.

Figure 5:
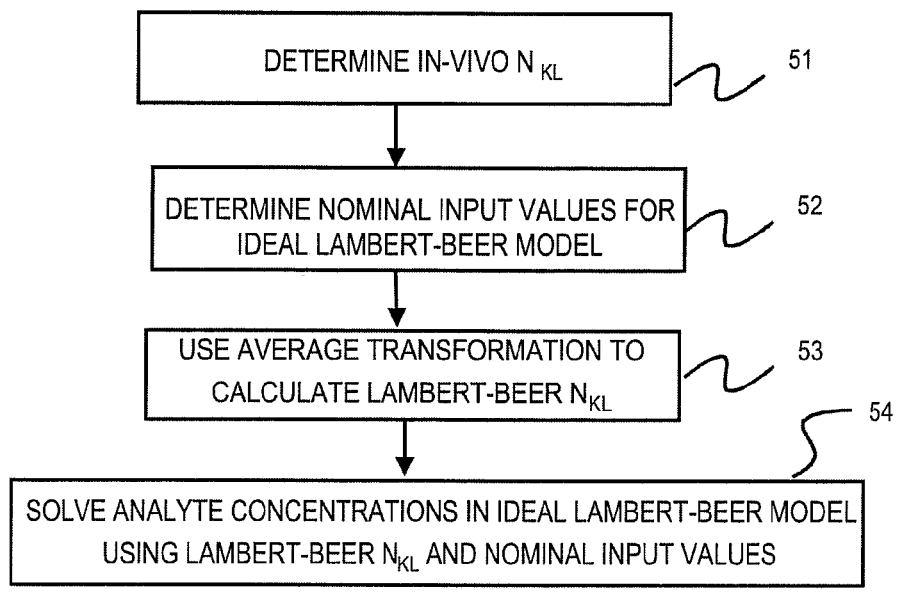
FIG. 5 is a flow diagram illustrating the prior art calibration method.

In a preferred embodiment of the invention, the radiation emitting means are Light Emitting Diodes (LED), but lasers emitting at one single wavelength are also possible. For lasers the effective extinction values are the extinction values at the laser wavelength, which can depend, however, on the temperature of the emitter component. In the case of a laser, Eg. 6 is thus not needed to calculate the effective extinction value. In the preferred embodiment of the invention the emitter and detector means are located at the tissue site at which the radiation is transmitted through the tissue, but the radiation can also be conducted to and from the tissue site in a light conducting fiber or in equivalent conduction means. In this case Eg. 6 shall also include a term for the spectral transmission of the radiation conductor. A sensor utilizing light conducting fibers can be as shown in FIG. 5 of the above-mentioned U.S. Pat. No. 6,104,938.

The extinction coefficients can thus be calculated according to this equation by determining all the above factors, which depend on the actual wavelength values, i.e. the optical properties of the sensor components and the tissue term. However, as the task of determining the exact spectral value of Eg. 6 is not possible in connection with a real-time pulse oximeter measurement using only a few discrete wavelength bands, in practice the result of Eg. 6 has to be approximated. The compensation is based on determining nominal extinction coefficients and approximating their wavelength dependence in advance at the factory and using this information in the real measurement situation to approximate the final subject-specific extinction coefficients.

The compensation algorithm will now be presented for a 4-wavelength pulse oximeter according to FIG. 1, having four LEDs at nominal wavelengths of 627 nm, 645 nm, 670 nm, and 870 nm. The extinction matrix for RHb (first column), $HbO_2$, HbCO, and metHb (last column) and for the above four wavelengths (627 nm on top) is then nominally in L/(mmol*cm).

$$E_{kl}^0 = \begin{pmatrix} 1.132 & 0.1799 & 0.2734 & 3.575 \\ 0.9182 & 0.1124 & 0.1337 & 2.411 \\ 0.7353 & 0.0885 & 0.0550 & 0.5796 \\ 0.2071 & 0.2772 & 0.010 & 0.5754 \end{pmatrix} \quad (7)$$

This equation (7) describes the nominal extinction matrix for the particular sensor used in the in-vivo measurement. Thus the changes of the optical properties of the sensor components with respect to the sensor components in the nominal calibration can thus be directly incorporated into this extinction matrix, a new nominal extinction matrix for the particular sensor.

The above extinction coefficients have been calculated applying Eg. 6 at nominal LED drive temperature without the tissue filtering term tissue($\lambda$). It then represents a nominal extinction matrix for a SpO2 sensor before its attachment on the tissue site. This extinction matrix is then altered on the basis of the measured filtering effect caused by tissue, when the sensor is attached on the site.

Figure 6:
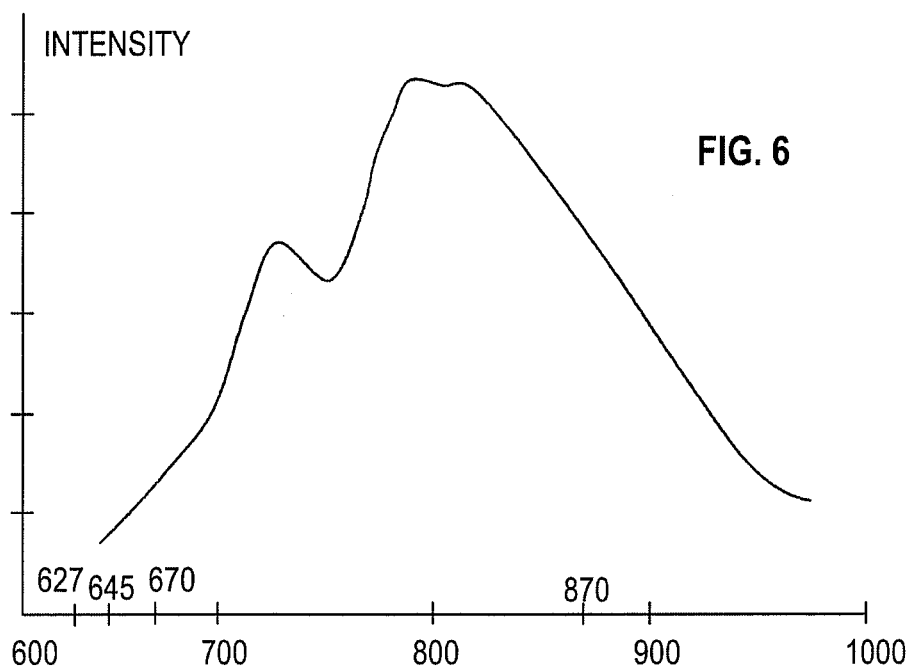
FIG. 6 illustrates an example of the transmission curve of human tissue, the curve being employed in the compensation of the inaccuracies caused by tissue-induced wavelength shift.

It is now assumed that the spectral tissue transmission is as presented in FIG. 6, which shows spectral characteristics of tissue in the same units for each wavelength, i.e. FLT as a function of the wavelength, based on an empirical measurement. In a continuous real-time SpO2 measurement, the transmission is known at 4 distinct wavelength values (the FLT values derived from the DC values in the pulse oximeter) marked in the figure. At each wavelength the slope of the tissue transmission curve can be determined or approximated using the four transmission values. The slope then determines the change in the tissue transmission in a band of a predetermined width (100 nm in this example) around the center of the LED band. We denote the slopes between 627 to 645 nm and 645 to 670 nm by A and B, respectively. This definition of the slopes is expressed as:

$$A = \frac{FLT(\lambda_2) - FLT(\lambda_1)}{(\lambda_2 - \lambda_1)*(FLT(\lambda_1) + FLT(\lambda_2))/2} * 100 \text{ and}$$

$$B = \frac{FLT(\lambda_3) - FLT(\lambda_2)}{(\lambda_3 - \lambda_2)*(FLT(\lambda_2) + FLT(\lambda_3))/2} * 100,$$

where $FLT(\lambda_j)$ is the measured FLT value determined at wavelength $\lambda_j$. The estimation of these slopes can be improved by calculating the curvature at the center LED (645 nm). This curvature (change of the slope/nm) is $$curv = \frac{B - A}{(\lambda_3 - \lambda_1)/2}.$$

Finally the expressions are obtained for the slopes s at the three red wavelengths using A and B as parameters:

$$\begin{pmatrix} s_{\lambda_1} \\ s_{\lambda_2} \\ s_{\lambda_3} \\ s_{\lambda_4} \end{pmatrix} = \begin{pmatrix} A - curv*(\lambda_2 - \lambda_1)/2 \\ (A + B)/2 \\ B + curv*(\lambda_3 - \lambda_2)/2 \\ -0.5 \end{pmatrix}, \quad (8)$$

where the slope at the IR wavelength has been estimated to be constant as it cannot be determined by the other LEDs. If we had had another LED, at about 800-1000 nm range, for example, it could have been used for the estimation of the IR slope. Because the extinction curves are very flat at 870 nm and the transmission is usually rather high, the tissue prefilter cannot alter the effective extinction coefficient from its nominal value significantly. The approximation of a constant transmission slope is thus considered sufficient.

In principle these slopes could be inserted in Eg. 6 in order to integrate the new true values for the extinction coefficients. However, this is impractical to do in real-time, so a simpler algorithm is presented below. We first calculate off-line the relative changes of extinction coefficients for each analyte of the system using Eg. 6 and assuming that the value of the slope equals a predetermined value, which is one in this example. This calculation (assuming the slope is 1) results in a shift matrix of Eq. 9:

$$Tissue_{SHIFT}^{SLOPE=1} = \begin{pmatrix} 0.975 & 0.942 & 0.940 & 0.999 \\ 0.984 & 0.966 & 0.920 & 0.916 \\ 0.963 & 0.986 & 0.896 & 0.789 \\ 1.01 & 1.03 & 0.903 & 1.05 \end{pmatrix}, \quad (9)$$

where the effective extinction of $HbO_2$ at 645 nm is 0.966 times the original value, and the effective extinction of HbCO at 670 nm is 0.896 times the original value, for example. The proportional change of the extinction coefficient is thus the matrix value minus one, i.e. ($Tissue^{SLOPE=1}-1$). Thus, the matrix of Eq. 9 defines the relative changes caused by the tissue, assuming that the slope of the tissue transmission curve equals one. During in-vivo measurement, the slope is continuously estimated using the DC values. The ratio of the slopes then indicates the relative change of a coefficient. In other words, if the relative slope is s, the relative change is $s*(Tissue^{SLOPE=1}-1)$. The relative changes are different for different analytes since the extinction coefficients of the different analytes behave differently as a function of wavelength.

In real-time the effective extinction coefficients can thus be calculated as follows:

$$E^{Eff} = E_{kl}^0 \otimes (1 + S \cdot (Tissue_{SHIFT}^{SLOPE=1} - 1)) \quad (10)$$

where S denotes the column array in Eq. 8 and the matrix multiplications are performed element by element ($\otimes$) or element by row ($\cdot$), respectively.

b) Compensating for Temperature Effect to Extinction Coefficient Values

Changes that the external temperature and the LED drive power induce to the nominal extinction coefficients must also be corrected. If the LEDs are not driven at the nominal drive currents, their effective wavelength may also be shifted by the temperature change at the LED p-n junction. The wavelength shift induced by temperature is typically about 0.1-0.2 nm/° C. which is significant if the drive currents are high, as is usually the case at wavelengths shorter than 660 nm. Thus, the extinction matrix of Eq. 10 must also be compensated for in varying LED drive conditions.

There are many ways to find out the temperature of the LED p-n junction. One alternative is to add a temperature sensor on the LED substrate and use the reading of the sensor for the compensation of all LED emission wavelengths. Though the junction temperature follows the substrate temperature according to some empirical heat conduction model, the method may be unreliable because the LED chip contact to the substrate and the internal heat conductivity may vary considerably. A better way is therefore to determine the junction temperature directly from the forward voltage drop of the LED junction. The junction has typical diode characteristics, which can be determined off-line for each LED separately after assembling the LEDs on the substrate. It is even possible to measure, with an optical spectrometer the shift of the emission as a function of the LED forward voltage. Relating the wavelength shift to the forward voltage assumes that the forward voltage is measured during the operation of the pulse oximeter. The circuit board of the pulse oximeter should thus preferably have means for performing the forward voltage measurement. But if it does not, the LED emission shift can be calibrated against the temperature sensor at the substrate. The LED manufacturer specifications for the temperature shift can then be used to calculate the corresponding wavelength shift. Still another practical compensation for the emitter temperature changes is to map empirically the relationship of the emitter drive current to the observed wavelength shift and to use this information to adjust the in-vivo extinction coefficients for the sensor.

A method for temperature compensation of the LED emission is now presented, assuming that the LED forward voltage is measured on the circuit board. The wavelength shifts can then be calculated as follows $$\begin{pmatrix} \Delta\lambda_1 \\ \Delta\lambda_2 \\ \Delta\lambda_3 \\ \Delta\lambda_4 \end{pmatrix} = \begin{pmatrix} k_1 \\ k_2 \\ k_3 \\ k_4 \end{pmatrix} \cdot \begin{pmatrix} \Delta V_1 \\ \Delta V_2 \\ \Delta V_3 \\ \Delta V_4 \end{pmatrix}, \quad (11)$$

where the shift coefficients $k_i$ are values determined empirically in advance and $\Delta V_L$ are the measured changes of the forward voltage drops. For the 627-645-670-870 nm LEDs of the sensor, the k-values are 0.06 nm/mV, 0.06 nm/mV, 0.09 nm/mV, and 0.1 nm/mV, respectively.

As in the compensation discussed above relating to tissue filtering, it is practical to first calculate the change in the extinction coefficients off-line for a certain fixed wavelength shift. In this example the relative changes of the extinction coefficients are calculated, as in Eq. 9, for a 5 nm wavelength shift for each of the four hemoglobin derivatives. The following shift matrix is then obtained:

$$Temp_{SHIFT}^{\Delta\lambda=5\,nm} = \begin{pmatrix} 0.919 & 0.820 & 0.798 & 0.974 \\ 0.963 & 0.926 & 0.823 & 0.794 \\ 0.941 & 0.983 & 0.855 & 0.725 \\ 1.0 & 1.01 & 0.963 & 1.02 \end{pmatrix}. \quad (12)$$

During in-vivo measurement, which will be later applied to a patient in a hospital or like, the relative changes are then calculated based on the measured wavelength shift. The ratio of the wavelength shifts then indicates the relative change of a coefficient caused by temperature. In other words, if the relative change calculated for a wavelength shift of Y1 is r, the relative change for the measured (in-vivo) wavelength shift of Y2 is $r_x$(Y2/Y1). The relative changes are different for different analytes, since the extinction coefficients of the different analytes behave differently as a function of wavelength.

The temperature compensated extinction coefficients are thus:

$$E_{TEMP}^{EFF} = E_{kl}^0 \otimes (1 + (\Delta\lambda/5\,nm) \cdot (Temp_{SHIFT}^{\Delta\lambda=5nm} - 1)) \quad (13),$$

where $\Delta\lambda$ is the array in Eq. 11. As mentioned earlier, $\Delta\lambda$ can also be estimated by reading the temperature indicated by the temperature sensor on the LED substrate or by measuring the LED drive current and using the mapping of the current to the wavelength shift.

The compensation of the variability causing wavelength shift type interference can now be summed up as follows:

$$E^{Eff} = E_{kl}^0 \otimes (1 + S \cdot (Tissue_{SHIFT}^{SLOPE=1} - 1)) \otimes (1 + (\Delta\lambda/5\,nm) \cdot (Temp_{SHIFT}^{\Delta\lambda=5nm} - 1)) \quad (14)$$

c) Compensating for Tissue Effect to Transformation Functions

The second compensation (the internal mechanism) controls the value of the transformation used to transform the modulation ratios $N_{kl}^{in-vivo}$ to the Lambert-Beer model $N_{kl}^{L-B}$. Therefore nominal transformation values are first calculated based on DC signals obtained from the sensor when the tissue properties are averaged over a large group of people. Then, in the actual in-vivo measurement subject-specific transformation values, i.e. individual tissue characteristics affecting the transformation values of a patient are calculated. Finally, based on the in-vivo measurement, the nominal transformation values are corrected, whereupon the corrected values are input to the transformations used to transform the modulation ratios to the Lambert-Beer model.

A practical implementation of the second compensating step is now discussed by introducing a new variable called "path length multiplier", since this will provide an easy way of understanding the technique in accordance with the invention.

As mentioned above, the purpose of the invention is to improve the accuracy of a pulse oximeter in situations in which the blood volume, the red blood cell density or the hematocrit, the total hemoglobin (g/dl), the division between the arterial and venous blood compartment volumes, and the arterial-venous saturation difference vary and produce human variability, which worsens the accuracy of the SpO2 measurement. It is also the purpose of the invention to compensate for the effect of skin pigmentation (dark skin), which in part can be considered to belong to the tissue prefilter category of compensations, but which also influences via modifying the path length multiplier. This modification is especially important for SpO2 ear sensors, which are attached to a very thin and pigmented tissue part (of about the same thickness corresponding to the diffusion constant in human tissue).

The interdependence of the above-described transformation and the path length multiplier is first illustrated by considering the photon path lengths through a single layer of artery blood and examining how the scattering and absorption affect it. It is postulated here that multiple scattering effectively increases the photon path length through the artery and that the absorption of the surrounding tissue effectively decreases it. In this way the artery and tissue are in interaction with each other. To derive a mathematical formulation of this relationship, the known Kubelka-Munk two-flux model can be used. This model defines an absorption probability K as follows:

$$K = \left\langle \frac{dl}{dz} \right\rangle * \Sigma_a, \quad (15)$$

where $\Sigma_a$ is the macroscopic absorption cross-section of the media and dl is the true average photon path length through the scattering and absorbing medium of infinitesimal layer thickness dz. The term $\langle dl/dz \rangle = K/\Sigma_a$ is a path length multiplier (plm) which enhances the arterial blood absorption from that of the Lambert-Beer non-scatter value because of the multiple scattering in the surrounding medium.

The idea of the path length multiplier is applied to the Lambert-Beer formulation of 2-λ pulse oximetry. The ratio of the change in absorption at the two probe wavelengths is defined as:

$$\frac{dA_k}{dA_l} = N_{kl}^{in-vivo} = \frac{\mu_a^k * d_k}{\mu_a^l * d_l}, \quad (16)$$

where $\mu_a^i$ is the arterial (non-scatter) absorption coefficient at wavelength i and $d_i$ is the effective true optical path length. The transformation is defined by substituting equation 15 with $dl=d_i$ in equation 16:

$$N_{kl}^{in-vivo} = \frac{\mu_a^k * \left(\frac{K}{\Sigma_a}\right)_k * dz}{\mu_a^l * \left(\frac{K}{\Sigma_a}\right)_l * dz} = \frac{\left(\frac{K}{\Sigma_a}\right)_k}{\left(\frac{K}{\Sigma_a}\right)_l} * N_{kl}^{ideal}, \quad (17)$$

where the ideal Lambert-Beer model is used for $N_{kl}^{ideal} \equiv \mu_a^k/\mu_a^l$, and where the layer thickness dz is the same for all wavelengths (k, l). Equation 17 now represents the transformation $(g_{kl})^{-1}$ from $N_{kl}^{in-vivo}$, i.e. from the measured value, to $N_{kl}^{L-B}$, which is the ratio of differential absorptions that would be measured if the measurement system were the ideal cuvette system of the Lambert-Beer model. For the transformation the equation below is obtained:

$$g_{kl} = \frac{\left(\frac{K}{\Sigma_a}\right)_k}{\left(\frac{K}{\Sigma_a}\right)_l} = \frac{plm_k}{plm_l}. \quad (18)$$

Thus the transforming quantity is a ratio of path length multipliers measured at two different wavelengths (k and l). The dependence of the function $g_{kl}$ thus refers to the absorption density of the scattering tissue in the surrounding of the infinitesimal arterial layer dz including the layer itself. This essentially means that the transformation does not require knowledge of the analyte composition in the arterial blood, but refers rather to the macroscopic light absorption, i.e. transmission through the tissue part under the sensor. That is in the language of pulse oximetry the DC component of the light transmission. This is utilized in the compensation of the invention.

Modifying Eq. 1 and leaving the attenuation of the probe design factors (i.e. CTR values) out of consideration, the relationship of the DC light transmission through the tissue and the path length multiplier can be presented as follows:

$$I_{out} = I_{in} e^{-\epsilon DC} = I_{in} e^{-plm\,D1\,C} \quad (19),$$

where D is the actual path length through the sample, D1 is the shortest path length through the sample (i.e. the thickness of the sample), and $\epsilon$ is the ideal extinction coefficient of the analyte. Here the $I_{out}/I_{in}$ can be associated with the FLT at the wavelength in question. Plm thus describes the internal attenuation factors in the tissue and, in particular, the enhancement of the absorbancy relative to the ideal cuvette absorption.

In nominal conditions, the path length multiplier has a certain nominal value $plm^0$ (where the superscript '0' refers to the nominal value). This nominal value can be determined in the factory at the manufacturing stage of the pulse oximeter. When the DC component is measured again in connection with in-vivo measurement, the change in the plm from the nominal value can be used to determine the change in the average transformation.

The term $\alpha_{int}$ in Eg. 4 can be expressed with the help of the path length multiplier in the Lambert-Beer model as $$\alpha_{int} = plm * \Sigma_a,$$

where $\Sigma_a$ accounts for all internal absorption sources and is defined in the non-scatter Lambert-Beer domain. The FLT at wavelength k can then be written as follows:

$$FLT_k = \exp(-\alpha_{int} * d) = \exp(-plm * \Sigma_a * d) \quad (20).$$

We then ratio the logarithms of the FLTs at two wavelengths k and l, which results in Eq. 21:

$$\frac{\log(FLT_k)}{\log(FLT_l)} = \frac{plm_k * \Sigma_a^k}{plm_l * \Sigma_a^l} \quad (21)$$

$$= g_{kl} * \frac{f_a * \mu_a^k + f_v * \mu_v^k}{f_a * \mu_a^l + f_v * \mu_v^l}$$

$$= g_{kl} * \frac{f_a * (\mu_a^k - \mu_v^k) + \mu_v^k}{f_a * (\mu_a^l - \mu_v^l) + \mu_v^l},$$

where $g_{kl} = plm_l/plm_k$ is the transformation between the Lambert-Beer and in-vivo modulation ratios according to Eq. 18, and in which the internal absorbing tissue compartments are venous and arterial blood with volume fractions $f_v$ and $f_a$ and with absorption coefficients $\mu_v$ and $\mu_a$ determined in the Lambert-Beer domain, respectively. In the last expression we have used for the venous volume fraction the relationship $f_v = 1 - f_a$. As the arterial volume fraction is always smaller than the venous volume fraction and as the arterial-venous absorption difference is always smaller than the venous absorption, the dominating factor in the last term is $\mu_v^k/\mu_v^l$, i.e. the venous saturation SvO2.

Thus the changes in the FLT and SvO2 from their nominal values provide the compensation needed for estimating the correct transformation function $g_{kl}$. We can then finally write for the relative change of the transformation function $g_{kl}$:

$$\frac{g_{kl}}{g_{kl}^0} = \frac{\log(FLT_k)}{\log(FLT_l)} \bigg/ \frac{\log(FLT_k)^0}{\log(FLT_l)^0} \bigg/ F_{kl}(SvO2, SaO2, f_a)/F_{kl}(SvO2, SaO2, f_a)^0, \quad (22)$$

where the function $F_{kl}$ represents the ratio term $$\frac{f_a(\mu_a^k - \mu_v^k) + \mu_v^k}{f_a(\mu_a^l - \mu_v^l) + \mu_v^l}$$

in Eq. 21 and the superscript 0 represents the nominal values of the nominal calibration function $g_{kl}^0$, which is on average true for a large patient population. In fact, the log(FLT) and the $F_{kl}$ compensation terms account for quite different human variability factors in the tissue: whereas $F_{kl}$ mainly tracks the changes of the arterial venous saturation difference, in particular SvO2, the log(FLT) reflects the changes in the total absorption of the tissue, i.e. in the total blood volume and the total hemoglobin or hematocrit, which are not seen in $F_{kl}$ at all. In practice, the largest corrections to the transformation function are due to the log(FLT) and $F_{kl}$ is less important.

The FLT in Eq. 22 is easily obtained at the two wavelengths k and l, as has been described earlier in Eg. 5. The function $F_{kl}$ k, represents the ratio of the absorption coefficients (in the Lambert-Beer non-scatter model) of the whole tissue at these same two wavelengths, i.e. it represents the internal color of the tissue. This internal absorption ratio can be measured by examining the low frequency baseline fluctuations of the plethysmographic wave signal.

Figure 14:
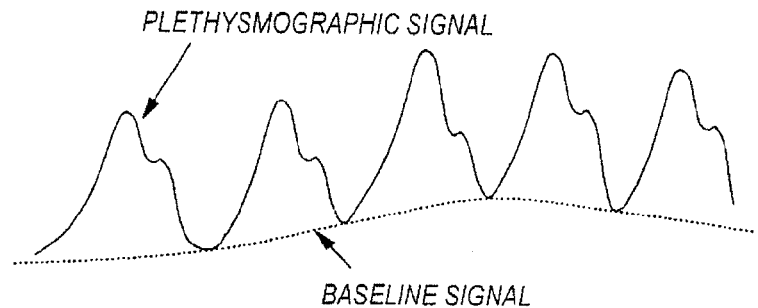
FIG. 14 depicts frequency baseline fluctuations of a plethysmographic wave signal.

FIG. 14 depicts frequency baseline fluctuations of the plethysmographic wave signal. These fluctuations are caused by the low frequency changes (usually of respiration origin) in the blood volume or in the blood volume distribution of the tissue. Similarly, since the arterial color (=R-ratio) is defined as the ratio of the arterial absorption coefficients, function $F_{kl}$ can be calculated as:

$$F_{kl} = \frac{f_a(\mu_a^k - \mu_v^k) + \mu_v^k}{f_a(\mu_a^l - \mu_v^l) + \mu_v^l} = g_{kl}^{-1}\left(\frac{(AC/DC)_k}{(AC/DC)_l}\right) = g_{kl}^{-1}(N_{kl}^{baseline}), \quad (23)$$

where AC is the amplitude (or the instantaneous slope) of the low frequency baseline fluctuation, instead of the heart pulse amplitude of the plethysmographic wave, and DC is the DC light transmission at that particular wavelength. Because the effective tissue color is mainly determined by the venous blood, function $F_{kl}$ can be approximated as the arterial modulation ratio calculated for the venous saturation, which is usually about SaO2−10% i.e. $F_{kl}$=R(SvO2=SaO2−10%).

If the venous saturation is determined by venous blood samples and the arterial saturation by the arterial blood samples, the function $F_{kl}$ can be calculated using the real blood values (with the assumption that the corresponding blood compartment volumes are $f_a$=0.25 and $f_v$=0.75).

Preferred Embodiment of the Invention

Figure 7:
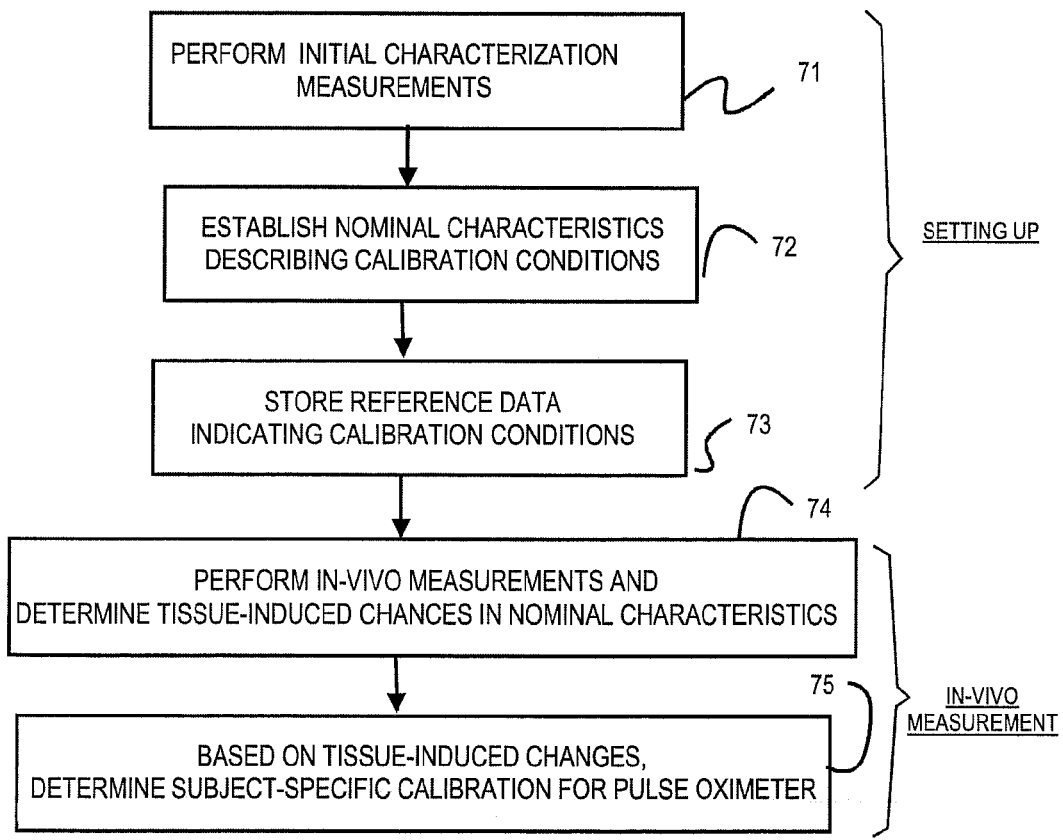
FIG. 7 is a flow diagram illustrating the general principle according to the present invention.

FIG. 7 is a flow diagram illustrating the general principle of the present invention. The method can be divided into two groups of phases. The first group 71-73 comprises measures relating to the setting up that is carried out prior to actual use of a pulse oximeter for measuring analyte concentrations of a patient whereas the second group 74-75 comprises method phases performed in the actual use. Previously in the present application the phases of the first group were also called off-line phases.

In the setting up phase, initial characterization measurements are first made, preferably at the calibration stage of the pulse oximeter with a nominal wavelength pulse oximeter sensor (phase 71). Based on the measurements, nominal characteristics are established describing the conditions under which the pulse oximeter has been calibrated (phases 72). As a result of these phases, reference data are stored (phase 73), which describe the calibration conditions of the pulse oximeter. In connection with subsequent in-vivo measurements, the same characteristics are again estimated and tissue-induced changes in the characteristics are determined based on the measured characteristics and the reference data stored (phase 74). In addition to the tissue induced changes, the changes relating to the different sensor than in the calibration stage are incorporated with the tissue changes. In in-vivo measurement, the $N_{kl}^{in-vivo}$ values are determined from the $dA_t$ values measured. On the basis of the changes determined, the subject-specific calibration is then determined (phase 75) for the in-vivo measurements to be performed by the pulse oximeter on the subject.

It is to be noted here that phases 71-73 are performed either when the pulse oximeter has been calibrated in a known manner or at the manufacturing stage of the pulse oximeter sensor when the sensor characteristics are determined. After these phases, the nominal transformation and the nominal extinction coefficients are known to the pulse oximeter Next, referring to FIG. 8-11 contents of phases 71 and 72 will be explained in more detail.

Figure 8:
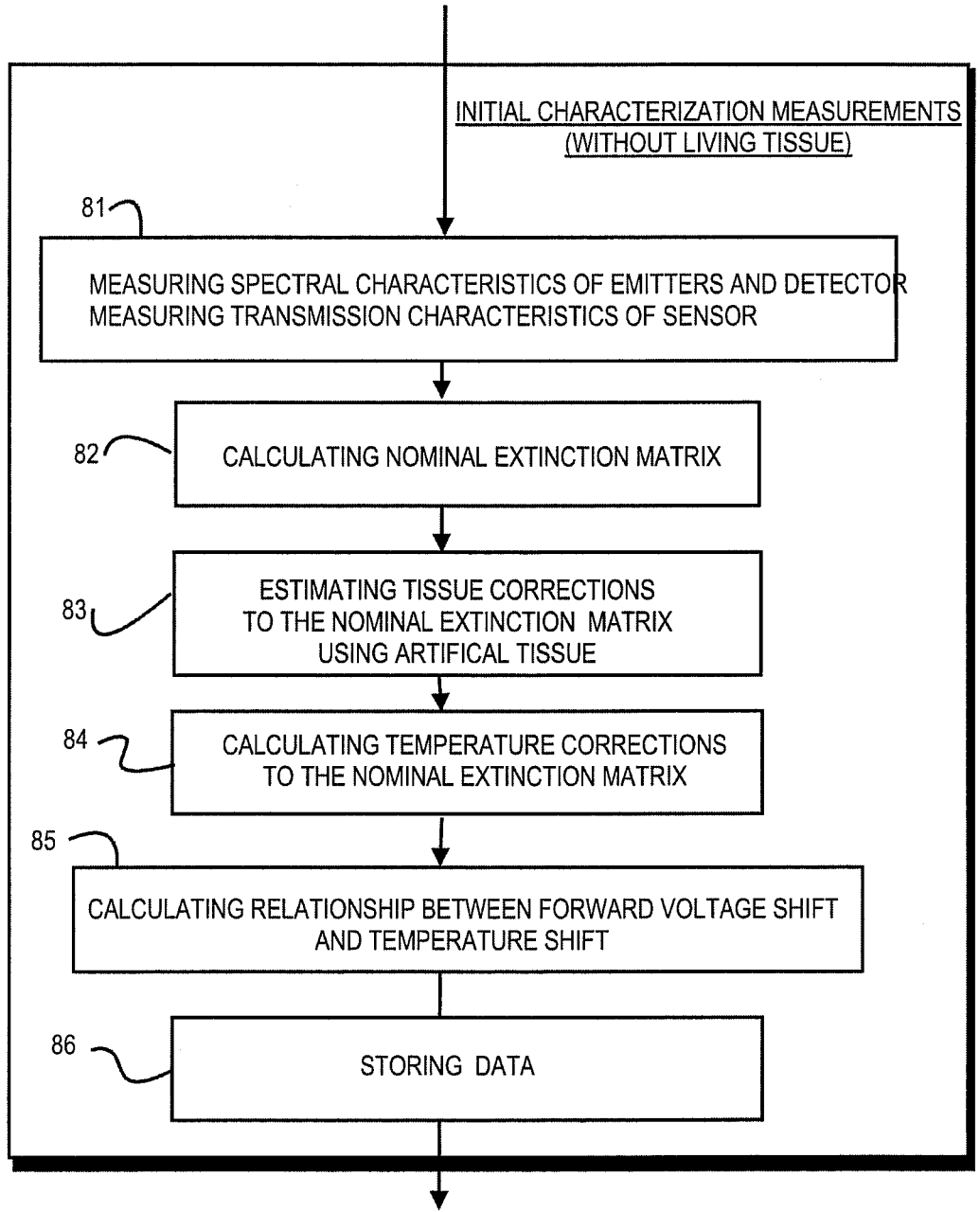
FIG. 8 is a flow diagram illustrating steps of initial characterization measurement phase.

FIG. 8 depicts the first steps carried out in the initial characterization phase of the setting up. It should be noted that in this phase no living tissue is needed. These steps are performed prior to the actual measurements, for example in the factory at the manufacturing stage of the pulse oximeter sensor. Thus, referring to FIG. 8, the steps are as follows.

Step 81.

Figure 13:
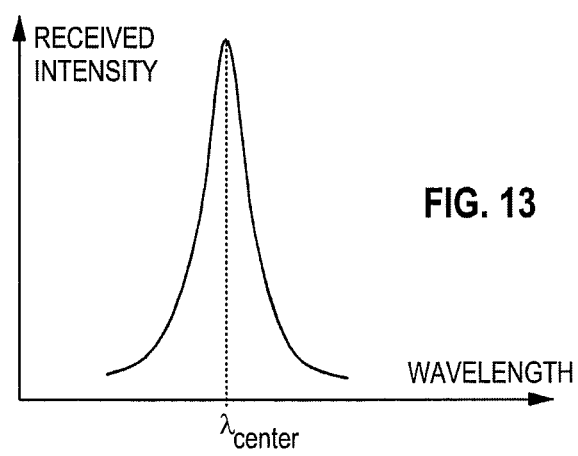
FIG. 13 depicts received intensity as a function of wavelength.

The spectral characteristics of the emitter/detector system are measured. In other words, the LEDs are characterized for their light emission (the emission as a function of wavelength) and the detector for its spectral sensitivity. This step thus includes determination of the characteristics of the curve shown in FIG. 13, i.e. the received intensity as a function of wavelength (at least around the wavelengths used). The light transmission from the light emitter to the light detector is measured without living tissue, i.e. the CTR is determined in the sensor in a fixed setup mimicking the actual use of the sensor. For clip-type sensors this is usually the Probe Off position of the sensor. The step also includes determination of the center wavelength of each LED.

Step 82

Using the spectral characteristics obtained at the previous step, the effective extinction coefficients for the nominal extinction matrix are determined without the tissue term. Thus in this step Eg. 6 is used without the tissue term (tissue ($\lambda$)) to form the nominal extinction matrix $E_{kl}^0$ according to Eg. 7.

Step 83

The tissue correction to the nominal extinction matrix is estimated for artificial tissue, in which transmission slopes are 1. In other words, the relative changes in the effective extinction coefficients due to artificial tissue filter effect are determined. Here Eg. 6 is used assuming that the slope of tissue($\lambda$) equals a predetermined fixed value at each wavelength. In other words, the shift matrix of Eq. 9 is determined.

Step 84

Temperature corrections to the nominal extinction matrix are determined, i.e. the relative changes in the effective extinction coefficients due to wavelength shift caused by changes in temperature are determined. In other words, the matrix of Eq. 12 is determined, which indicates the relative changes for a wavelength shift of a predetermined value. Said value could be 5 nm, for example.

Step 85

If the LED forward voltage method is used, the LED forward voltages are characterized at a typical drive current for small ambient temperature changes. In other words, the relationship between the forward voltage shift and the temperature shift is established for each emitter. Thus, the temperature coefficients k, in Eq. 11 and the nominal forward voltage drops at nominal temperature are determined for each LED.

Step 86

All data obtained in the previous steps are saved in a memory unit in the sensor or in the control unit, or the corresponding information is otherwise made available to the pulse oximeter, for example, by using codes, such as sensor identification numbers, which indicate the values of the information.

As is obvious from the above, steps 81 to 86 include performing initial characterization measurements for the compensation, said measurements to include measuring the light transmission of the apparatus, establishing nominal DC transmission characteristics of the apparatus on the basis of the measurements, and for subsequent in-vivo measurements storing reference data that indicate the transmission characteristics established.

Thus, in these first initial characterization measurements, the value of Eg. 6 is determined using nominal values, and the nominal extinction matrix is formed. The apparatus is also provided with the data needed in the subsequent in-vivo compensation steps for calculating the changes in the factors included in Eg. 6. In the in-vivo steps the said changes are determined and a new extinction matrix is formed, whereby the new extinction values are such that the external effects are compensated for.

To sum up, after the setting up steps the pulse oximeter stores the matrices according to equations 7, 9, and 12 and the values of the shift coefficients $k_i$. In addition to this, the oximeter stores the CTR values and the center wavelengths corresponding to these values.

Figure 9:
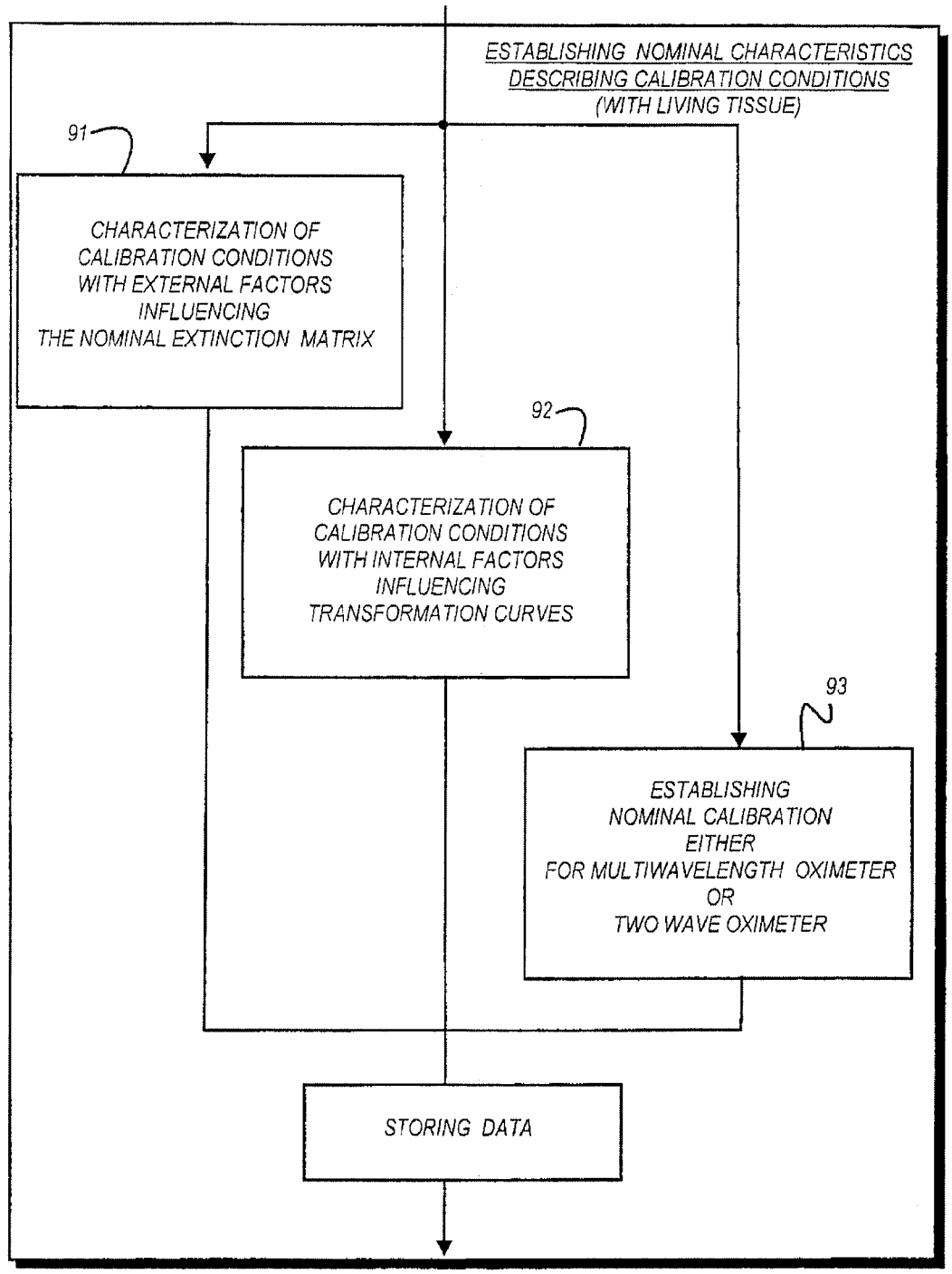
FIG. 9 depicts stages of the phase of establishing nominal characteristics.

FIG. 9 depicts setting up stages that are carried out while establishing calibration and nominal characteristics, which describe calibration conditions (phase 72 in FIG. 7). These setting up stages consist of three measurement and calculation stages that are carried out simultaneously. Stage 91 includes characterization of calibration conditions when external factors influence the nominal extinction matrix that was formed previously. Stage 92 includes characterization of calibration conditions when internal factors influence transformation curves. Stage 93 includes establishment of nominal calibration either for multiwavelength pulse oximeter of two-wave pulse oximeter. In performing the steps the information stored during initial characterisation measurements (phase 71 in FIG. 7) is utilized. In addition, it is worth noting that when doing the measurements in said three steps a sensor is attached to the pulse oximeter and there is living tissue between the emitters and the detector. As to living tissues, a large group of people is used in order to obtain enough statistical data. At least the nominal calibration and the nominal internal factors are stored. Optionally external factors are stored.

FIG. 10 is a block diagram depicting different steps of stage 91 (FIG. 9). The content of the steps are as follows:

Step 101

The forward voltage drops ($\Delta V$) are measured for each LED and for each subject in a group of people. The voltage drops are compared with the nominal drops obtained in step 85 of FIG. 8 or the temperature is compared with the nominal temperature. The change in the forward voltage relative to the sensor nominal values are calculated, the nominal values having been stored in the sensor memory unit or in the control unit memory. If the pulse oximeter does not have forward voltage measuring means, the temperature of each LED is estimated by reading the temperature indicated by a sensor on the LED substrate, and either the manufacturer specifications or empirical data for corresponding wavelength changes or a look-up table mapping the emitter drive current to the center wavelength shift is used.

Step 102

Then the change in the extinction matrix for the temperature compensation is calculated. This is done for each person of the group. Calculation is done according to Eq. 11-13, i.e. using the wavelength shifts determined according to Eq. 11 and calculating the matrix of Eq. 13 using the matrices of Eg. 7 and 12 stored in step 84 of FIG. 8.

Step 103

For each person of the group the tissue transmission induced changes to the nominal extinction matrix are calculated. Thus, the DC light transmission for each LED channel (wavelength) is measured, and the value measured is normalized to an emitter current value of 1 mA. The result is the FCTR of the sensor. An estimate for the FLT is then calculated for each emitter (wavelength). In this connection, the FLT values are used for calculating the slopes (A and B). In other words, all DC values are normalized in relation to the 1 mA emitter current in order to make all values comparable to one another. Equations 8-10 are used for calculating the change of the nominal extinction matrix.

Step 104

This step is an alternative to the next step. Namely it might be practical simply to average the results obtained in the previous steps for each person of the group and then just combine the average values (temperature and tissue effects) into one extinction matrix.

Step 105

If step 104 is omitted, then the effective Lambet-Beer extinction matrix for each person of the group is calculated. The effective Lambert-Beer extinction coefficients are determined using Eq. 14. Thus, each of those matrices characterizes the calibrations conditions for one particular person of the group.

Step 106

Averaging of the individual Lambet-Beer matrices element by element results in a group average extinction matrix that characterize the extinction coefficients during the nominal calibration process.

Optionally all the data is stored. However, it may be more practical that in the subsequent in-vivo pulse oximeter measurements the steps 101-106 are continuously repeated to update extinction matrix coefficients using only the information stored in the setting-up phase of FIG. 8. When the data describing the external factors—mainly the characteristics relating to the sensor—is stored, it can be used for checking up the sensor condition and alert the user if considerable, abnormal deviation from the average characteristics occur during in-vivo measurements. The stored data can thus be used to issue a Probe Fault Condition alarm.

Next, referring to FIG. 11 the content of the stage 92 (FIG. 9) is explained. As stated above, that stage is performed simultaneously with stages 91 and 93.

Step 111

Characterization of the calibration conditions with internal factors influencing transformation curves starts by first fetching the FLTs calculated in step 103 of FIG. 10 and then by calculating the ratio of the logarithms for each wavelength pair and for each person of the group. In other words, the nominal light transmission through a finger or ear lobe or its approximation at the distinct nominal wavelengths of the sensor, is determined for each person of a group (the group may be a population of patients or volunteers or even for only one single volunteer), on whom the nominal calibration was performed. This gives for each person of the group an individual curve $$\frac{\log(FLT_k)^0}{\log(FLT_l)^0}$$

as a function of $N_{kl}^{in\text{-}vivo}$ at these wavelengths (k,l), i.e. essentially as a function of the correct SpO2.

Step 112

A regression curve is calculated from the individual curves obtained in step 111. The logarithm ratios fitted to the regression curve and the corresponding $N_{KL}$ values are stored in the table 1, 5$^{th}$ column. The table is presented below. This information is stored in the sensor memory unit (or in the control unit).

Step 113

F-factors, i.e. function $F^0$ can be determined in two alternative ways:

a) In the above measurement using the baseline fluctuations, $N_{kl}^{baseline}$ is calculated and transformed to the Lambert-Beer model by the nominal transformation $(g^0_{kl})^{-1}$ for the group of persons (patients or volunteers or even for only one single volunteer, on whom the nominal calibration was performed). This is tabulated in table 1 below as a function of $N_{kl}^{in-vivo}$ at these wavelengths (k, l). These data are stored in the sensor memory unit (or in the control unit).

b) In the above measurement venous and arterial blood samples are taken from a position close to the sensor site and analyzed for RHb, HbO$_2$, HbCO, and metHb. The absorption coefficients $\mu_a$ and $\mu_v$ are then calculated using the measured analyte fractions. The arterial volume fraction $f_a$ is then estimated. Usually it is sufficient to approximate that $f_a$ is equal to 0.25. The functions $F_{kl}^0$ are calculated in the Lambert-Beer Model using the venous and arterial volume fractions and $$\mu_{a,v} = RHb*\mu_{a,v}^{RHb} + HbO2*\mu_{a,v}^{HbO2} + HbCO*\mu_{a,v}^{HbCO} + metHb*\mu_{a,v}^{metHb}.$$

As a result of steps 111-113, we have set up a look-up table for each wavelength pair, in which the following nominal information is tabulated:

TABLE 1

| k | l | $N_{kl}^{in-vivo}$ | $g_{kl}^0$ | $Log(FLT_k)^0/log(FLT_l)^0$ | $g_{kl}^{-1} \times (N_{kl}^{baseline})$ | $F^0kl$ |
|---|---|---|---|---|---|---| and where also the nominal transformation $g^0$ is presented and $N_{kl}^{baseline} \cong g_{kl}^0 = (F_{kl})$. Only one of the two last columns is necessary, depending on the way the values of function F are determined. It is also to be noted that the ratio is not necessary in column 5, but that it is enough to store the FLT values from which the ratio of their logarithms can be calculated.

As is obvious from the above, steps 111-113 again include measuring the DC light transmission of the apparatus, establishing nominal DC transmission characteristics for the apparatus on the basis of the measurements, and storing reference data for subsequent in-vivo measurements, the data indicating the transmission characteristics established.

After the above setting up steps, which can be performed at the manufacturing stage of the pulse oximeter, the pulse oximeter is ready for use in a hospital environment or like in connection with in-vivo measurements.

Now, next we consider a case where the pulse oximeter is used to detect blood oxygenation of a patient in a hospital or like, i.e. in-vivo measurement is to be performed. The patient puts his finger of ear lobe between the emitters and the detector whereupon light transmission through the finger or ear lobe is measured. The sensor of the pulse oximeter produces data that is processed as shown in FIG. 12. It is worth noting that during the measurement pulsative signals are collected through the whole measuring period. Accordingly, the full round of steps that will be described below are performed cyclically many times, one round per each pulsation of the heart, for example.

FIG. 12 shows four steps of the data processing in the in-vivo measurement. Firstly, changes that patient tissue causes to the nominal extinction matrix are calculated, step 121. Secondly, changes that patient tissue causes to the nominal transformation curves are calculated, step 122. Thirdly, the nominal values, which were calculated in the setting up phase, are compared with the individual patient values calculated. Equation 22 is used to get the individual transformation function for the patient (step 123). Finally, the individual transformation functions obtained from step 123 and the individual extinction matrix obtained from step 121 are applied to Lambert-Beer model that gives analytic concentrations of the patient.

The steps are now explained in more detail.

Step 121 is actually repetition of steps 101-102 of FIG. 10. Thus, the forward voltage drops ($\Delta V$) are measured for each LED. The voltage drops are compared with the nominal drops stored in the memory. The change in the forward voltages relative to the sensor nominal values is calculated. Then the change in the nominal extinction matrix for the temperature compensation is calculated. Calculation is done according to Eq. 11-13, i.e. using the wavelength shifts determined according to Eq. 11 and calculating the matrix of Eq. 13 using the matrices of Eg. 7 and 12. Calculation in step 121 therefore results in patient specific extinction matrix.

Accordingly, step 122 is actually repetition of step 111 of FIG. 11. The step starts by first fetching the FLTs stored in the memory during the setting up process of the oximeter and then by calculating the ratio of the logarithms for each wavelength pair and for the patient. In other words, the nominal light transmission through the finger or ear lobe is determined for the patient. This gives for the patient a curve $$\frac{\log(FLT_k)}{\log(FLT_l)}$$

as a function of $N_{kl}^{in-vivo}$ at these wavelengths (k, l). Then in Table 1 in the row where the measured modulation ratio at the wavelengths k and l equals $N_{kl}^{in-vivo}$, the nominal $$\frac{\log(FLT_k)^0}{\log(FLT_l)^0}$$

is read. The correction factor $$\frac{\log(FLT_k)}{\log(FLT_l)} \bigg/ \frac{\log(FLT_k)^0}{\log(FLT_l)^0}$$

is then calculated.

Then in step 123, comparison between the nominal values stored in Table 1 and the individual patient specific values obtained from step 112 is done and equation (22) is used to get the patient specific transformation functions. This is carried out so that in Table 1 in the row, where the measured modulation ratio at the wavelengths k and l equals $N_{kl}^{in-vivo}$, the nominal $F_{kl}^0$ is read from either of the last two columns. Then the correction factor $F_{kl}/F_{kl}^0$ is determined in one of the following two ways:

a) Column $g^{-1} \times (N^{baseline})$: By using the baseline fluctuations of the measured plethysmographic wave and by using Eq. 23 with $g^{-1}$, the function $F_{kl}$ is determined. The correction factor $F_{kl}/F_{kl}^0$ is then calculated. For determining $N^{baseline}$ and its changes, the amplitudes of the signal can be used, as is normally done for a modulation ratio N.

b) Column $F_{kl}$: The blood analytes RHb, HbO$_2$, HbCO, and metHb are solved in the Lambert-Beer model using the nominal transformation $g^0$. This is the first approximation for the analytes. The absorption coefficients $\mu_a$ and $\mu_v$ are calculated using the measured analyte fractions in the arterial absorption and approximating the absorption coefficient in the venous blood by using the measured dyshemoglobin fractions and setting $HbO2^{vena}=HbO2-10\%$ and $RHb^{vena}=RHb+10\%$, where $f_a=0.25$ is assumed. The functions $F_{kl}$ are calculated in the Lambert-Beer Model using the equation:

$$\mu_{a,v}=RHb*\mu_{a,v}^{RHb}+HbO2*\mu_{a,v}^{HbO2}*HbCO*\mu_{a,v}^{HbCO}+metHb*\mu_{a,v}^{metHb}.$$

A new transformation $g_{kl}$ is calculated using Eq. 22, and the new transformation is used for solving the analyte concentrations in the Lambert-Beer model. Optionally, a more accurate estimate of $F_{kl}$ can be obtained by iteration of new analyte fractions for the new corrected transformation.

Finally, in step 124 the patient specific transformation functions and the patient specific extinction matrix are used to solve the analyte concentrations by applying them to the Lambert-Beer model.

During the above steps 121-124 in-vivo measurements are performed, wherein the DC component of the radiation emitted through the tissue and received by the detector is measured, tissue-induced changes in the transmission characteristics are determined based on the in-vivo DC component and the transmission characteristics stored, and on the basis tissue-induced changes the subject-specific variation in the in-vivo measurement is compensated for.

The above setting up and in-vivo steps compensate for the non-ideal characteristics of the broadband emitters or for external effects on the light source emission spectra. They do also compensate for the variation in the absorption and scattering interplay in the tissue, i.e. the internal effects, which equally influence a single line laser emitter and a broadband LED emitter. Lasers also show shifts in the emission line wavelength as a function of the temperature. Therefore, the lasers are compensated for the temperature and internal tissue effects, but not for the pre-filter tissue-induced spectral shifts.

The pre-calculated data utilized by the pulse oximeter can be stored in the sensor part of the pulse oximeter, whereby the same sensor can be attached to different pulse oximeter housings.

Figure 15:
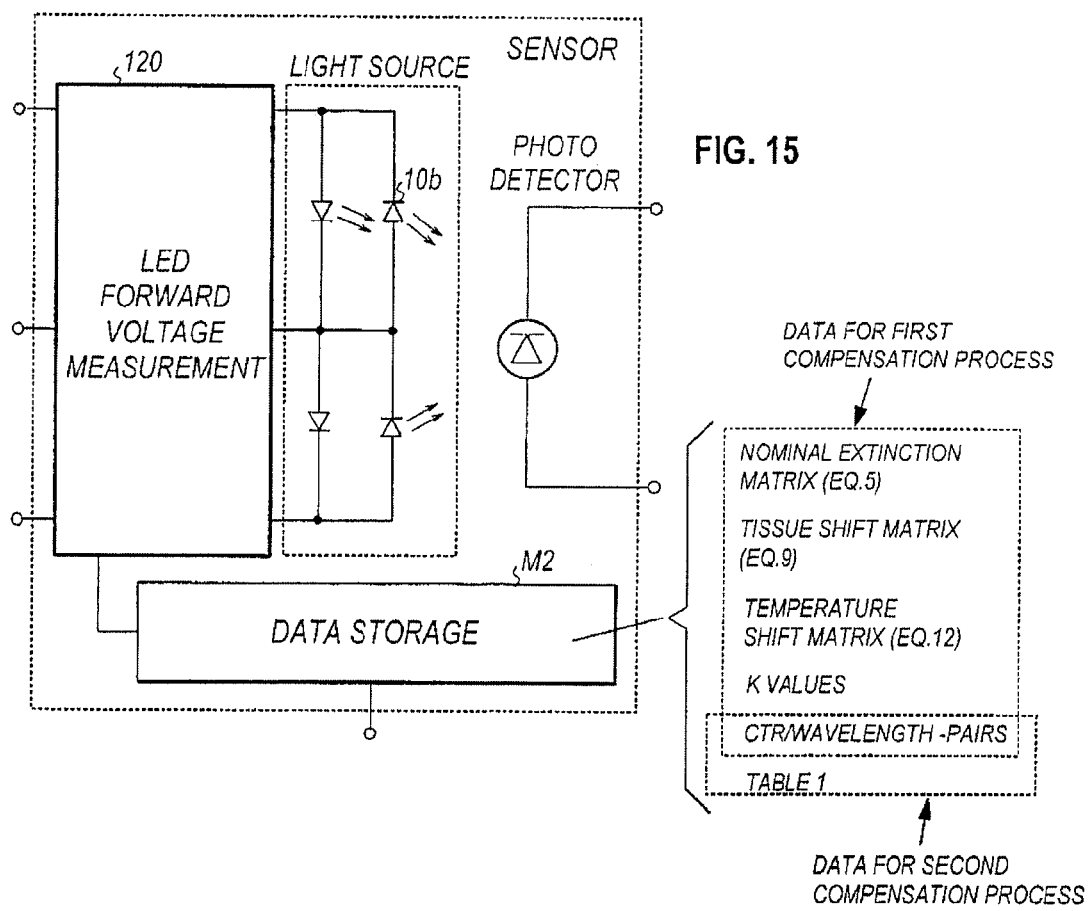
FIG. 15 illustrates an embodiment of a sensor according to the invention.

FIG. 15 illustrates the general structure of a sensor according to the invention, the detailed configuration of the sensor being dependent on which information is stored in the sensor and which in the signal processing part, and also on the amount of the calculation appropriate in the signal processing part.

Nevertheless, a sensor according to the invention includes the light sources (10a-10c) and the photo detector, the light sources being adapted to emit at two or more wavelengths. In addition, the sensor includes a data storage unit M2 for storing the data on the basis of which the signal processing part can perform the above-described calibration. The information necessary for the above compensations is shown in the figure. For the first compensation process the pulse oximeter needs the k-values, the above-mentioned three matrices, i.e. the nominal extinction matrix (Eg. 7), the shift matrices (Eqs. 9 and 12), and the CTR/wavelength pairs. For the second compensation process, in turn, the pulse oximeter needs the information stored in Table 1 and the CTR/wavelength pairs. As mentioned above, at least part of this data determined prior to the use of the device for in-vivo measurements can also be stored in the control unit part of the pulse oximeter. The apparatus further preferably includes means 150 for measuring the forward voltage of the p-n junction of each LED, as discussed above.

Figure 16:
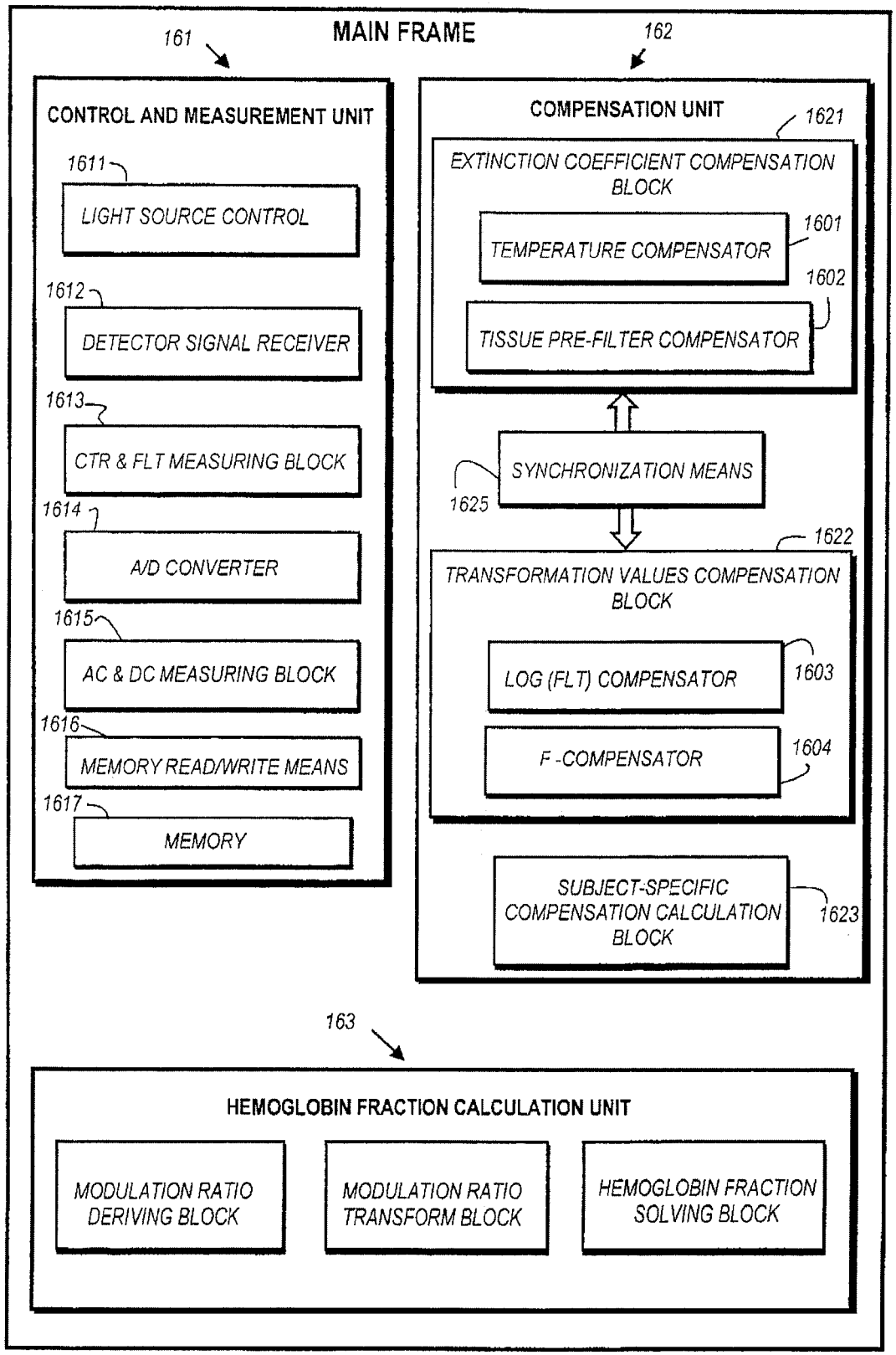
FIG. 16 illustrates main frame blocks of a pulse oximeter.

FIG. 16 illustrates the general structure of a main frame. The main frame refers here to hardware loaded with software, which are enclosed in the housing ox a pulse oximeter. The main frame comprises three units: control and measurement unit 161, compensation unit 162 and hemoglobin fraction calculation unit 163.

Control and measurement unit 161 includes light source controller 1611 that forms and controls supply current to the emitters of the light source. The emitters locate in the separate sensor (see FIG. 15). Detector signal receiver 1612 receives the signal from the photo detector, filters and amplifies said signal. The amplified analog signal is converted to digital domain in A/D converter 1614 whereupon AC and DC components are separated from the digital signal. Further, the control and measurement unit 161 also includes memory read/write means 1616 for storing data in and reading data from memory 1617 in the main frame and memory in the sensor. Control and measurement unit 161 per se is known in the art except the module 1613, in which the sensor CTR and the functional light transmission are measured.

The inventive part of the main frame resides mainly in compensation unit 162 that includes software to perform the method steps of the invention. The unit 162 comprises of extinction compensation block 1621, path length multiplier compensation block 1622, and block 1623 for calculating subject specific compensation.

Extinction compensation block 1621 includes software adapted to create a nominal extinction and to correct said matrix by compensating it for tissue pre-filter effects and temperature effect. In other words, tissue pre-filter compensator 1601 calculates an amount of tissue pre-filtering compensation that is needed and temperature compensator 1602 calculates an amount of the needed temperature compensation. Thus, the blocks 1601 and 1602 are adapted to perform the steps described under subtitles (a) and (b).

Path length multiplier compensation block 1622 is adapted to control the value of the transformation used to transform the modulation ratios $N_{kl}^{in-vivo}$ to the Lambert-Beer model $N_{kl}^{L-B}$. Thus, the block performs operations described previously under subtitle (c). Log (FLT) compensator 1603 fetches the FLTs, that have been calculated in block 1612, and then calculates the ratio of the logarithms for each wavelength pair and for each person of a group. Then this block calculates the relative change of the nominal transformation function. F-compensator 1605 14 calculates function $F_{kl}$ that can be approximated as the arterial modulation ratio calculated for the venous saturation.

The last block of the compensation unit 1621 is a block that calculates subject-specific compensation based on the results of a in-vivo measurement and the data stored in memory 1617.

The results obtained from block 1623 are fed to hemoglobin fraction calculation unit 163 that is per se known from the prior art.

Figure 17:
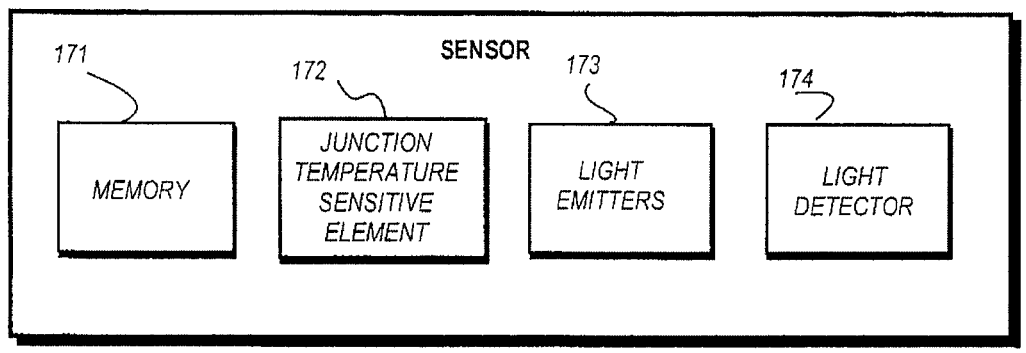
FIG. 17 illustrates main blocks of a sensor.

FIG. 17 depicts some units of the sensor. The sensor comprises memory 171 for storing data, particularly the reference data indicating calibration conditions, i.e. data produced by the compensation unit 162. Optionally reference data may also be stored in memory 1617 residing in the main frame of a pulse oximeter. For calculating a correction to the nominal extinction matrix, which is required pursuant to a wavelength shift caused by a temperature change in the emitter chip, the sensor is provided with junction sensitive element 172. The element monitors the temperatures of the pn-junctions of the LEDs and produces signals to be fed to the main frame. Further, the sensor includes light emitters 173 and 174.

As can be seen from the above, the method of the invention is based on the DC transmission of light. By means of the DC measurements in the setting up phase, reference data is first created. During subsequent in-vivo DC measurements, the reference data is then utilized to filter out human variability from the in-vivo measurement.

Although the method in accordance with the invention has been discussed in connection with a four wavelength pulse oximeter, it can also be employed in a basic two wavelength pulse oximeter. However, the method is more beneficial in a multi-wavelength pulse oximeter where the number of analytes to be measured is greater than two.

In the case of a two-wavelength pulse oximeter, the simplest way to apply the compensation is first to formulate the calibration of the two-wavelength oximeter as a first step using only one transformation function $g^{-1}$ (e.g. at wavelengths 660 nm and 900 nm) and a second step using a two-times-two extinction matrix $\epsilon$ for these wavelengths and for the two analytes RHb and HbO2. The compensation procedures are then identical to the ones presented in the above multi-wavelength method. If the calibration of the two-wavelength pulse oximeter is done in the normal way using a direct mapping of the in-vivo measured R-ratio ($=N_{660-900}$) to the SpO2 percentage, the compensation steps could for example, be as follows: The wavelength shifts from the nominal LED center wavelength values to a change in the SpO2 value can first be coded. The wavelength shifts are determined for the temperature component as described in the above multi-wavelength method and for the tissue component by mapping at the two wavelengths the change in the FLT ratio from its nominal value in the calibration conditions to a change in the SpO2 value from the nominal calibration SpO2. The tissue wavelength shift cannot be estimated as accurately as in the multi-wavelength oximeter, but sufficient compensation to the tissue prefilter can still be obtained and the accuracy of the pulse oximeter can be improved. The last compensation step also includes the compensation for the internal tissue variability, which is summed with the prefilter effect.

A distinguishing feature of the invention is that compensation is made several times during the in-vivo measurement. In other words, the pulse oximeter measurement is compensated heartbeat-by-heartbeat, i.e. the oxygenation measurement is accurate for each patient and for each time moment in the individual patient. This is not known from the prior art. Further, the same apparatus is used both in the calibration phase, the initial characterization with tissue and the in-vivo characterization with tissue. The method compensates continuously and dynamically the tissue induced changes and keeps the PO measurement accurate at all times. The apparatus and method is also used in the manner that the same apparatus is suitable both the in-vivo characterization and the tissue characterization during the calibration. The prior art technology uses different techniques in the initial characterization and in-vivo characterization.

Although the invention has been described above with reference to the examples shown in the appended drawings, it is obvious that the invention is not limited to these, but may be modified by those skilled in the art without departing from the scope and spirit of the invention. For example, instead of transformation, any other quantity by which the pulse oximeter can correct the average calibration known to it can be used to eliminate human variability.

The invention has also been described with reference to pulse oximeters for analytes which are in the blood of a subject. The invention, however, can also be applied at different wavelength ranges, e.g. at around 1.5 µm for glucose, at which similar compensation means are called for. The other substances in the tissue modify the effective extinction of the glucose because they alter the path length multiplier at this wavelength. Similarly, the tissue prefilter and temperature effects are taken into account.

The invention claimed is:

1. A method for compensating for subject-specific variability in a pulse oximeter intended for non-invasively determining in in-vivo measurement the amount of at least two light-absorbing substances in the blood of a subject and provided with emitters for emitting radiation at a minimum of two different wavelengths and with a detector for transforming the radiation received into an electrical output signal, the method comprising the steps of measuring a detector output signal when living tissue of the subject is present between the emitters and the detector in a sensor, wherein the detector output signal depends on the tissue, reading from a memory a nominal calibration comprising nominal extinction matrix $E_{kl}^0$, reading from the memory nominal characteristics describing conditions under which the nominal calibration has been done, the nominal characteristics comprising:

nominal values for a calculation defining tissue-induced correction to the nominal extinction matrix $E_{kl}^0$ due to light transmission through living tissue, nominal values for a calculation defining temperature-induced corrections to the nominal extinction matrix $E_{kl}^0$ due to wavelength shifts caused by changes in emitter temperatures, establishing values for both calculations for the sensor on the living tissue of the subject using the detector output signal, forming a subject-specific calibration by correcting the nominal extinction matrix $E_{kl}^0$ with both calculations with the established values, solving hemoglobin fractions using the corrected nominal extinction matrix in a Lambert-Beer model.

2. The method as in claim 1, wherein the calculation defining tissue-induced correction is a matrix operation according to the equation $$E^{Eff} = E_{kl}^0 \otimes (1 + (\Delta\lambda/5 \text{ nm}) \cdot (\text{Temp}_{SHIFT}^{\Delta\lambda=5nm} - 1))$$

where $E_{kl}^0$ is included in the nominal calibration, S denotes a column array in:

$$\begin{pmatrix} s_{\lambda_1} \\ s_{\lambda_2} \\ s_{\lambda_3} \\ s_{\lambda_4} \end{pmatrix} = \begin{pmatrix} A - \text{curv} * (\lambda_2 - \lambda_1)/2 \\ (A+B)/2 \\ B + \text{curv} * (\lambda_3 - \lambda_2)/2 \\ -0.5 \end{pmatrix}$$

and the matrix multiplications are performed element by element ($\otimes$) or element by row ($\cdot$), respectively.

3. The method as in claim 1, wherein the calculation defining temperature-induced correction is a matrix operation according to the equation $$E_{TEMP}^{EFF} = E_{kl}^0 \otimes (1 + (\Delta\lambda/5 \text{ nm}) \cdot (\text{Temp}_{SHIFT}^{\Delta\lambda=5nm} - 1))$$

where $\Delta\lambda$ is an array in:

$$\begin{pmatrix}\Delta\lambda_1\\\Delta\lambda_2\\\Delta\lambda_3\\\Delta\lambda_4\end{pmatrix} = \begin{pmatrix}k_1\\k_2\\k_3\\k_4\end{pmatrix} \cdot \begin{pmatrix}\Delta V_1\\\Delta V_2\\\Delta V_3\\\Delta V_4\end{pmatrix}$$

and $\text{Temp}_{SHIFT}^{\Delta\lambda=5nm}$ is as in:

$$\text{Temp}_{SHIFT}^{\Delta\lambda=5\,nm} = \begin{pmatrix}0.919 & 0.820 & 0.798 & 0.974\\0.963 & 0.926 & 0.823 & 0.794\\0.941 & 0.983 & 0.855 & 0.725\\1.0 & 1.01 & 0.963 & 1.02\end{pmatrix}.$$

4. The method as in claim 1, wherein the established values for the calculation defining tissue induced correction to the nominal extinction matrix $E_{kl}^{o}$ due to light transmission through living tissue are derived from Functional Light Transmission Signals FLT for each emitter.

5. The method as in claim 1, wherein new values for a ratio of absorption coefficients in the Lambert-Beer model are calculated on the basis of measured fluctuation of a DC component of the radiation received by the detector.

6. The method according to claim 1, wherein all the method steps are performed at each heartbeat of the subject.

* * * * *

UNITED STATES PATENT AND TRADEMARK OFFICE
CERTIFICATE OF CORRECTION

PATENT NO. : 8,515,514 B2
APPLICATION NO. : 12/233251
DATED : August 20, 2013
INVENTOR(S) : Huiku It is certified that error appears in the above-identified patent and that said Letters Patent is hereby corrected as shown below:

In the Claims

Replace Claim 2 with the following rewritten claim:

The method as in Claim 1, wherein the calculation defining tissue-induced correction is a matrix operation according to the equation $$E^{Eff} = E^0_{kl} \otimes (1 + S \bullet (Tissue^{SLOPE-1}_{SHIFT} - 1))$$

where $E^0_{kl}$ is included in the nominal calibration, $S$ denotes a column array in:

$$\begin{pmatrix} s_{\lambda_1} \\ s_{\lambda_2} \\ s_{\lambda_3} \\ s_{\lambda_4} \end{pmatrix} = \begin{pmatrix} A - curv * (\lambda_2 - \lambda_1)/2 \\ (A+B)/2 \\ B + curv * (\lambda_3 - \lambda_2)/2 \\ -0.5 \end{pmatrix}$$

and the matrix multiplications are performed element by element ($\otimes$) or element by row ($\bullet$), respectively.

Signed and Sealed this
Fourth Day of March, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,515,514 B2
APPLICATION NO. : 12/233251
DATED : August 20, 2013
INVENTOR(S) : Huiku It is certified that error appears in the above-identified patent and that said Letters Patent is hereby corrected as shown below:

In the Claims

Column 5, lines 12-14, replace Claim 2 with the following rewritten claim:

The method as in Claim 1, wherein the calculation defining tissue-induced correction is a matrix operation according to the equation $$E^{\text{eff}} = E_{kl}^0 \otimes (1 + S \bullet (Tissue_{SHIFT}^{SLOPE \cdot l} - 1))$$

where $E_{kl}^0$ is included in the nominal calibration, $S$ denotes a column array in:

$$\begin{pmatrix} s_{\lambda_1} \\ s_{\lambda_2} \\ s_{\lambda_3} \\ s_{\lambda_4} \end{pmatrix} = \begin{pmatrix} A - curv * (\lambda_2 - \lambda_1)/2 \\ (A+B)/2 \\ B + curv * (\lambda_3 - \lambda_2)/2 \\ -0.5 \end{pmatrix}$$

and the matrix multiplications are performed element by element ($\otimes$) or element by row ($\bullet$), respectively.

This certificate supersedes the Certificate of Correction issued March 4, 2014.

Signed and Sealed this
Twenty-fifth Day of March, 2014

Michelle K. Lee
*Deputy Director of the United States Patent and Trademark Office*